US011206991B2

(12) United States Patent
Oberlin et al.

(10) Patent No.: US 11,206,991 B2
(45) Date of Patent: Dec. 28, 2021

(54) SYSTEMS AND METHODS FOR PROCESSING LASER SPECKLE SIGNALS

(71) Applicant: Activ Surgical, Inc., Boston, MA (US)

(72) Inventors: John Oberlin, Boston, MA (US); Emanuel Demaio, Boston, MA (US)

(73) Assignee: ACTIV SURGICAL, INC., Boston, MA (US)

( * ) Notice: Subject to any disclaimer, the term of this patent is extended or adjusted under 35 U.S.C. 154(b) by 0 days.

(21) Appl. No.: 17/245,374

(22) Filed: Apr. 30, 2021

(65) Prior Publication Data

US 2021/0251502 A1     Aug. 19, 2021

Related U.S. Application Data

(63) Continuation of application No. PCT/US2021/018008, filed on Feb. 12, 2021.
(Continued)

(51) Int. Cl.
*A61B 5/026* (2006.01)
*G02B 27/48* (2006.01)
(Continued)

(52) U.S. Cl.
CPC .......... *A61B 5/0261* (2013.01); *A61B 5/0059* (2013.01); *A61B 5/72* (2013.01); *G02B 27/48* (2013.01); *A61B 34/37* (2016.02)

(58) Field of Classification Search
CPC .......... G06T 7/00; G06T 7/90; G06T 7/0012; G06T 2207/30104; G06T 2207/10004;
(Continued)

(56) References Cited

U.S. PATENT DOCUMENTS 8,721,077 B2* 5/2014 Vermeer ............ G01B 9/02091
351/205
8,724,928 B2   5/2014 Deever
(Continued)

FOREIGN PATENT DOCUMENTS

CN     110301908 A   10/2019
WO  WO-2000058775 A1  5/2000
(Continued)

OTHER PUBLICATIONS

Vaz ["Laser Speckle Imaging to Monitor Microvascular Blood Flow: A Review", IEEE Reviews In Biomedical Engineering, vol. 9, 2016]. (Year: 2016).*
(Continued)

*Primary Examiner* — Oommen Jacob
(74) *Attorney, Agent, or Firm* — Wilson Sonsini Goodrich & Rosati

(57) ABSTRACT

The present disclosure provides systems and methods for processing laser speckle signals. The method may comprise obtaining a laser speckle signal from a laser speckle pattern generated using at least one laser light source that is directed towards a tissue region of a subject and a reference signal corresponding to a movement of a biological material of or within the subject's body. The method may comprise computing one or more measurements using a first function corresponding to at least the laser speckle signal and a second function corresponding to the reference signal. The method may comprise generating an output signal in part based on the one or more measurements for the function space and using the output signal to aid a surgical procedure on or near the tissue region of the subject.

20 Claims, 12 Drawing Sheets

Related U.S. Application Data

(60) Provisional application No. 63/022,147, filed on May 8, 2020, provisional application No. 63/021,914, filed on May 8, 2020, provisional application No. 62/976,669, filed on Feb. 14, 2020.

(51) Int. Cl.
*A61B 5/00* (2006.01)
*A61B 34/37* (2016.01)

(58) Field of Classification Search
CPC ........ G06T 2207/10024; A61B 5/0059; A61B 5/0075; A61B 5/0062; A61B 5/0261; A61B 5/445; A61B 1/042; A61B 5/0086; A61B 5/026; A61B 5/0093; A61B 5/1455; A61B 5/02416; H04N 1/482; H04N 1/6086; H04N 1/603; G01N 2021/479; G02B 27/00; G02B 27/48
See application file for complete search history.

(56) References Cited

U.S. PATENT DOCUMENTS

| | | | |
|---|---|---|---|
| 8,823,790 B2* | 9/2014 | Dunn | G02B 27/48 348/77 |
| 9,286,268 B2 | 3/2016 | Seeman et al. | |
| 9,962,090 B2* | 5/2018 | DiMaio | G16H 50/20 |
| 10,265,023 B2* | 4/2019 | Roh | G02B 27/48 |
| 10,600,183 B2 | 3/2020 | Barral et al. | |
| 2002/0183601 A1* | 12/2002 | Tearney | A61B 1/0615 600/310 |
| 2004/0102686 A1* | 5/2004 | Knudson | A61B 5/14546 600/309 |
| 2009/0177098 A1* | 7/2009 | Yakubo | G06T 7/0012 600/504 |
| 2009/0270702 A1* | 10/2009 | Zeng | A61B 5/1459 600/323 |
| 2011/0319775 A1* | 12/2011 | Fujii | A61B 3/1233 600/504 |
| 2012/0071769 A1* | 3/2012 | Dunn | G06T 5/009 600/504 |
| 2013/0165869 A1 | 6/2013 | Blumenkranz et al. | |
| 2013/0296715 A1 | 11/2013 | Lasser et al. | |
| 2014/0132752 A1* | 5/2014 | Edgar | H04N 5/253 348/97 |
| 2014/0316286 A1 | 10/2014 | Addison et al. | |
| 2015/0049178 A1* | 2/2015 | Dunn | G02B 27/48 348/77 |
| 2015/0198797 A1* | 7/2015 | Andre | G02B 21/16 348/80 |
| 2016/0328848 A1* | 11/2016 | Andre | H04N 1/482 |
| 2017/0017858 A1* | 1/2017 | Roh | G02B 27/48 |
| 2017/0202607 A1 | 7/2017 | Shelton, IV et al. | |
| 2017/0319073 A1* | 11/2017 | DiMaio | G16Z 99/00 |
| 2018/0025535 A1 | 1/2018 | Lessig et al. | |
| 2018/0296103 A1 | 10/2018 | Rege et al. | |
| 2019/0167118 A1 | 6/2019 | Vilenskii et al. | |
| 2021/0145295 A1* | 5/2021 | Fujita | A61B 5/026 |

FOREIGN PATENT DOCUMENTS

| | | |
|---|---|---|
| WO | WO-2018029123 A1 | 2/2018 |
| WO | WO-2019237013 A1 | 12/2019 |
| WO | WO-2020006454 A1 | 1/2020 |
| WO | WO2021163603 A1 | 8/2021 |

OTHER PUBLICATIONS

Humeau-Heurtier "Multiscale Entropy Study of Medical Laser Speckle Contrast Images" IEEE Transactions on Biomedical Engineering, vol. 60, No. 3, Mar. 2013 (Year: 2013).*
Briers, et al., Laser speckle contrast imaging: theoretical and practical limitations. Journal of Biomedical Optics 2013 18(6) 066018.
Drawer, et al., Review of laser speckle contrast techniques for visualizing tissue perfusion. Lasers Med Sci 2009 24:639-651.
Duncan, et al., Statistics of Local Speckle Contrast. Journal of the Optical Society of America, A, V. 25, pp. 9-15 (2008).
Jain, et al., Measuring light transport properties using speckle pattern structured illumination. Nature Scientific Reports 2019 9:11157. https://doi.org/10.1038/s41598-019-47256-8.
Kalchenko, et al., A robust method for adjustment of laser speckle contrast imaging during transcranial mouse brain visualization. Photonics 2019, 6(80); doi:10.3390/photonics6030080.
Postnikov, et al., Gaussian sliding window for robust processing laser speckle contrast images. Int J Numer Meth Biomed Engng 2019; 35:e3186. http://doi.org/10.1002/cnm.3186.
Ramirez-San-Juan et al., Spatial versus temporal laser speckle contrast analyses in the presence of static optical scatterers. Journal of Biomedical Optics 2014 19(10).
Song et al., Effect of signal intensity and camera quantization on laser speckle contrast analysis. Biomedical Optics Express 2013. vol. 4, No. 1.
PCT/US21/18008 International Search Report and Written Opinion dated Jun. 23, 2021.

* cited by examiner

SYSTEMS AND METHODS FOR PROCESSING LASER SPECKLE SIGNALS

CROSS REFERENCE

This application is a Continuation Application of International Patent Application PCT/US2021/018008, filed Feb. 12, 2021, which claims priority to U.S. Provisional Application No. 62/976,669 filed Feb. 14, 2020, U.S. Provisional Application No. 63/021,914 filed May 8, 2020, and U.S. Provisional Application No. 63/022,147 filed May 8, 2020, each of which is incorporated herein by reference in its entirety for all purposes.

BACKGROUND

Laser Speckle Contrast Imaging (LSCI) is an optical technique that uses laser light to illuminate a diffuse surface to produce a visual effect known as a speckle pattern. Image frames containing speckle patterns may be analyzed to compute dynamic and structural quantities of a target region or surface.

SUMMARY

Images of laser speckle patterns may be analyzed over a number of frames to quantify and/or observe one or more physical, chemical, structural, morphological, physiological, or pathological features and/or properties of a target region. Conventional systems and methods for laser speckle imaging processing may analyze laser speckle signals over a finite number of frames, which may be computationally intensive. The systems and methods of the present disclosure may be implemented to process laser speckle signals obtained over an infinite number of frames in order to quantify and/or observe various physical, chemical, structural, morphological, physiological, or pathological features and/or properties of a target region. Processing over an infinite number of frames may reduce computational overhead and may provide a more accurate, real-time method of processing speckle image frames by dynamically adjusting the weights and priorities of different computable values. The systems and methods of the present disclosure may also be implemented to verify and/or enhance different quantifiable or observable features and/or properties of the target region. The laser speckle processing systems and methods disclosed herein may analyze or process laser speckle signals in part by comparing the signals to one or more reference signals. The systems and methods of the present disclosure may allow a medical operator to determine which features in a laser speckle pattern are attributable to a movement of a biological material and which features in the laser speckle pattern are attributable to an external physical movement that is not necessarily associated with such movement of such biological material. The systems and methods of the present disclosure may allow a medical operator to distinguish between different movements caused by various materials and/or objects and filter or enhance different portions or features of a laser speckle pattern, signal, or image to make more accurate assessments or observations of a feature or property of a target region. The systems and methods of the present disclosure may be used to eliminate one or more false positives or false negatives that may be generated when attempting to process or analyze laser speckle patterns, images, and/or signals. The systems and methods of the present disclosure may also be used to interpret laser speckle patterns, images, and/or signals more accurately, and to detect critical structures that are not visible or easily detectable in laser speckle patterns or other images of a surgical scene. As an added benefit, the systems and methods of the present disclosure may be implemented to determine if a medical instrument or surgical tool is touching a target region, estimate an amount of force exerted when the tool is touching the target region, or compute an amount of tension in a thread that is being handled by a surgeon or robot.

In an aspect, the present disclosure provides a method for processing laser speckle signals. The method may comprise: (a) obtaining (1) a laser speckle signal from a laser speckle pattern generated using at least one laser light source that is directed towards a tissue region of a subject and (2) a reference signal corresponding to a movement of a biological material of or within the subject's body; (b) defining a function space based at least in part on a first function corresponding to at least the laser speckle signal; (c) computing one or more measurements for the function space, wherein the one or more measurements are defined in part based on a second function corresponding to the reference signal; (d) generating an output signal in part based on the one or more measurements for the function space; and (e) using the output signal to aid a surgical procedure on or near the tissue region of the subject.

In some embodiments, the function space corresponds to a set of functions associated with a set of laser speckle signals generated using the at least one laser light source. In some embodiments, the set of laser speckle signals comprises the laser speckle signal. In some embodiments, the laser speckle pattern is generated using a plurality of laser light sources configured to generate a plurality of laser beams or pulses having different wavelengths. In some embodiments, the plurality of laser beams or pulses have a wavelength between about 100 nanometers (nm) and about 1 millimeter (mm).

In some embodiments, the function space comprises a Lebesgue function space. In some embodiments, at least one of the first function and the second function comprises an infinite dimensional vector function comprising a set of output values lying in an infinite dimensional vector space.

In some embodiments, the laser speckle signal is obtained over a plurality of frames as the plurality of frames are being received or processed in real time.

In some embodiments, the one or more measurements for the function space are derived in part by comparing the first function and the second function. In some embodiments, comparing the first function and the second function comprises projecting the laser speckle signal onto the reference signal, or projecting the reference signal onto the laser speckle signal, to compare a first set of pixel values associated with the laser speckle signal against a second set of pixel values associated with the reference signal. In some embodiments, comparing the first function and the second function comprises computing at least one of an inner product, a dot product, a cross-correlation, an auto-correlation, a normalized cross-correlation, or a weighted measure integration using the first function and the second function. In some embodiments, comparing the first function and the second function comprises using one or more signal or time series comparators to determine an amount or degree of correlation between the first function and the second function. In some embodiments, the comparison of the first function and the second function is performed in a time domain or a frequency domain. In some embodiments, the comparison of the first function and the second function occurs over at least a portion of a laser speckle image comprising the laser speckle pattern, the portion corresponding to one or more regions of interest in or near the tissue region of the subject. In some embodiments, the comparison of the first function and the second function is performed substantially in real time and frame by frame for each new frame captured for a laser speckle image comprising the laser speckle pattern.

In some embodiments, the reference signal is obtained or generated using a pulse signal associated with a pulse of the subject. In some embodiments, the pulse signal is obtained using an external device. In some embodiments, the external device comprises a pulse oximeter.

In some embodiments, the method further comprises using the pulse signal to determine if one or more features of the laser speckle pattern are attributable to a fluid flow or a physical motion.

In some embodiments, the one or more measurements for the function space correspond to an amount or degree of correlation between the laser speckle signal and the pulse signal.

In some embodiments, the output signal comprises a flow signal that is usable to generate a perfusion flow map. In some embodiments, the flow signal is usable to eliminate one or more false positives in the perfusion flow map. In some embodiments, the one or more false positives correspond to one or more areas in the perfusion flow map that indicate a movement but do not have fluid flowing through the one or more areas.

In some embodiments, the reference signal is obtained or generated using a plurality of waveforms associated with vibrations of two or more motors that are configured to spin at different frequencies. In some embodiments, the two or more motors are housed in a transducer that is coupled to a surgical tool that is used to perform one or more steps of the surgical procedure. In some embodiments, the plurality of waveforms comprise a superposition of a first waveform with a first frequency and a second waveform with a second frequency that is different from the first frequency. In some embodiments, the superposition of the first waveform and the second waveform generates a pulsing waveform. In some embodiments, the first waveform comprises a carrier wave. In some embodiments, the carrier wave has a fixed or constant waveform. In some embodiments, the carrier wave has a variable waveform.

In some embodiments, the laser speckle signal comprises a modulated laser speckle signal that is generated when the surgical tool is placed in contact with the tissue region of the subject.

In some embodiments, the one or more measurements for the function space correspond to an amount or degree of correlation between the modulated laser speckle signal and the reference signal in a time domain or a frequency domain.

In some embodiments, the output signal comprises a flow signal that is usable to generate a perfusion flow map and determine if one or more features of the perfusion flow map are attributable to a fluid flow or a physical motion.

In some embodiments, the output signal comprises a force signal that is usable to determine if the surgical tool is touching the tissue region of the subject.

In some embodiments, the output signal comprises a force signal that is usable to determine an amount of force exerted on a tissue in or near the tissue region of the subject by the surgical tool when the surgical tool is placed in contact with the tissue region of the subject.

In some embodiments, the biological material comprises a fluid. In some embodiments, the fluid comprises blood, lymph, tissue fluid, milk, saliva, semen, bile, an intracellular fluid, an extracellular fluid, an intravascular fluid, an interstitial fluid, a lymphatic fluid, or a transcellular fluid. In some embodiments, the biological material comprises a tissue. In some embodiments, the tissue is in or near the tissue region.

In another aspect, the present disclosure provides a method for generating a perfusion flow map, the method comprising: (a) obtaining a laser speckle signal from a laser speckle pattern generated using at least one laser light source that is directed towards a tissue region of a subject; (b) generating a reference signal from a pulse signal associated with a pulse of the subject; (c) comparing the laser speckle signal to the reference signal; and (d) generating the perfusion flow map based in part on the comparison of the laser speckle signal to the reference signal.

In some embodiments, the method further comprises: using the comparison of the laser speckle signal to the reference signal to determine if one or more features of the laser speckle pattern are attributable to a fluid flow or a physical motion.

In some embodiments, the method further comprises: using the comparison of the laser speckle signal to the reference signal to eliminate one or more false positives in the perfusion flow map. In some embodiments, the one or more false positives correspond to one or more areas in the perfusion flow map that indicate a movement but do not have fluid flowing through the one or more areas.

In some embodiments, comparing the laser speckle signal to the reference signal comprises: (c1) defining a function space based at least in part on a first function corresponding to at least the laser speckle signal; and (c2) computing one or more measurements for the function space. In some embodiments, the one or more measurements are (i) defined in part based on a second function corresponding to the reference signal and (ii) used to generate the perfusion flow map.

In some embodiments, the function space corresponds to a set of functions associated with a set of laser speckle signals generated using the at least one laser light source. In some embodiments, the set of laser speckle signals comprises the laser speckle signal.

In some embodiments, the function space comprises a Lebesgue function space. In some embodiments, at least one of the first function or the second function comprises an infinite dimensional vector function comprising a set of output values lying in an infinite dimensional vector space.

In some embodiments, the one or more measurements for the function space are derived in part by comparing the first function and the second function. In some embodiments, comparing the laser speckle signal and the reference signal comprises projecting the laser speckle signal onto the reference signal, or projecting the reference signal onto the laser speckle signal, to compare a first set of pixel values associated with the laser speckle signal against a second set of pixel values associated with the reference signal. In some embodiments, comparing the first function and the second function comprises computing at least one of an inner product, a dot product, a cross-correlation, an auto-correlation, a normalized cross-correlation, or a weighted measure integration using the first function and the second function. In some embodiments, comparing the first function and the second function comprises using one or more signal or time series comparators to determine an amount or degree of correlation between the first function and the second function. In some embodiments, the comparison of the first function and the second function is performed in a time domain or a frequency domain. In some embodiments, the comparison of the first function and the second function occurs over at least a portion of a laser speckle image, the portion comprising one or more regions of interest in the laser speckle image. In some embodiments, the comparison of the first function and the second function is performed substantially in real time and frame by frame for each new frame captured for a laser speckle image comprising the laser speckle pattern.

In some embodiments, the one or more measurements for the function space correspond to an amount or degree of correlation between the laser speckle signal and the pulse signal. In some embodiments, the laser speckle signal is obtained over a plurality of frames as the plurality of frames are being received or processed in real time. In some embodiments, the laser speckle pattern is generated using a plurality of laser light sources configured to generate a plurality of laser beams or pulses having different wavelengths or frequencies. In some embodiments, the plurality of laser beams or pulses have a wavelength between about 100 nanometers (nm) and about 1 millimeter (mm).

In some embodiments, the method further comprises: using the perfusion flow map to determine if the tissue region comprises viable tissue that receives blood flow.

In some embodiments, the method further comprises: using the perfusion flow map to detect one or more critical structures that are not visible.

In another aspect, the present disclosure provides a method for determining a force exerted on a tissue that is in or near a tissue region of a subject, the method comprising: (a) obtaining a laser speckle signal from a laser speckle pattern generated using at least one laser light source that is directed towards the tissue region of the subject; (b) generating a reference signal using a plurality of waveforms associated with vibrations of two or more motors that are configured to spin at different frequencies; (c) modulating the laser speckle signal using the reference signal; (d) comparing the modulated laser speckle signal to the reference signal; and (e) generating a force signal based in part on the comparison of the modulated laser speckle signal to the reference signal.

In some embodiments, the two or more motors are housed in a transducer that is coupled to a surgical tool that is used to perform one or more steps of a surgical procedure.

In some embodiments, the modulated laser speckle signal is generated when the surgical tool is placed in contact with the tissue region of the subject.

In some embodiments, the plurality of waveforms comprise a superposition of a first waveform with a first frequency and a second waveform with a second frequency that is different from the first frequency. In some embodiments, the superposition of the first waveform and the second waveform generates a pulsing waveform. In some embodiments, the first waveform comprises a carrier waveform. In some embodiments, the carrier wave has a fixed or constant waveform. In some embodiments, the carrier wave has a variable waveform.

In some embodiments, the force signal is usable to determine if the surgical tool is touching a tissue that is in or near the tissue region of the subject. In some embodiments, the force signal is usable to determine an amount of force exerted on a tissue that is in or near the tissue region of a subject by the surgical tool when the surgical tool is placed in contact with the tissue region of the subject.

In some embodiments, comparing the modulated laser speckle signal to the reference signal comprises: (d1) defining a function space based at least in part on a first function corresponding to at least the modulated laser speckle signal; and (d2) computing one or more measurements for the function space, wherein the one or more measurements are (i) defined in part based on a second function corresponding to the reference signal and (ii) used to generate the force signal.

In some embodiments, the function space corresponds to a set of functions associated with a set of laser speckle signals generated using the at least one laser light source. In some embodiments, the set of laser speckle signals comprises the modulated laser speckle signal.

In some embodiments, the function space comprises a Lebesgue function space. In some embodiments, at least one of the first function or the second function comprises an infinite dimensional vector function comprising a set of output values lying in an infinite dimensional vector space.

In some embodiments, the one or more measurements for the function space are derived in part by comparing the first function and the second function. In some embodiments, comparing the modulated laser speckle signal and the reference signal comprises projecting the modulated laser speckle signal onto the reference signal, or projecting the reference signal onto the modulated laser speckle signal, to compare a first set of pixel values associated with the modulated laser speckle signal against a second set of pixel values associated with the reference signal. In some embodiments, comparing the first function and the second function comprises computing at least one of an inner product, a dot product, a cross-correlation, an auto-correlation, a normalized cross-correlation, or a weighted measure integration using the first function and the second function. In some embodiments, comparing the first function and the second function comprises using one or more signal or time series comparators to determine an amount or degree of correlation between the first function and the second function. In some embodiments, the comparison of the first function and the second function is performed in a time domain or a frequency domain. In some embodiments, the comparison of the first function and the second function occurs over at least a portion of a laser speckle image comprising the laser speckle pattern, the portion corresponding to one or more regions of interest in or near the tissue region of the subject. In some embodiments, the comparison of the first function and the second function is performed substantially in real time and frame by frame for each new frame captured for a laser speckle image comprising the laser speckle pattern.

In some embodiments, the one or more measurements for the function space correspond to an amount or degree of correlation between the modulated laser speckle signal and the reference signal in a time domain or a frequency domain. In some embodiments, the laser speckle signal is obtained over a plurality of frames as the plurality of frames are being received or processed in real time. In some embodiments, the laser speckle pattern is generated using a plurality of laser light sources configured to generate a plurality of laser beams or pulses having different wavelengths or frequencies. In some embodiments, the plurality of laser beams or pulses have a wavelength between about 100 nanometers (nm) and about 1 millimeter (mm).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
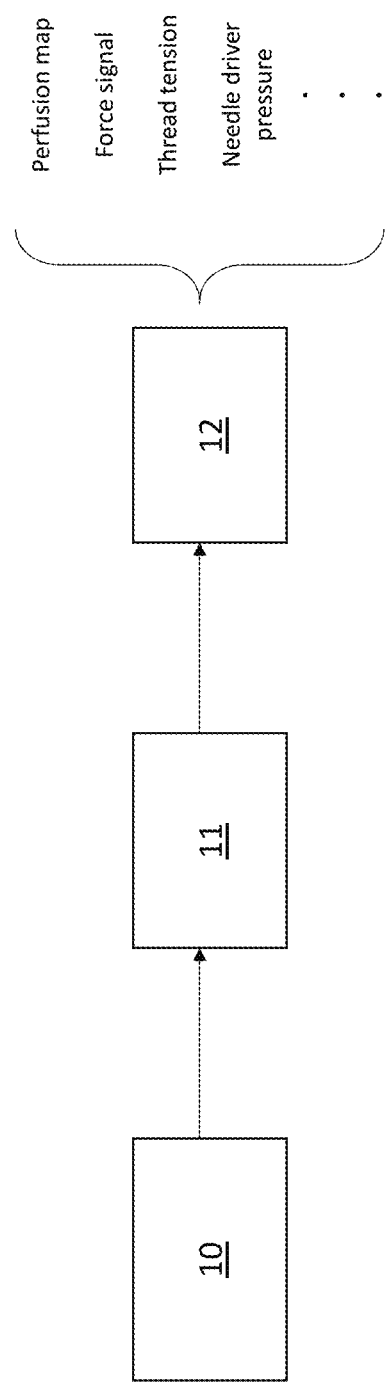
FIG. 1 schematically illustrates a system for processing laser speckles, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "real-time," as used herein, generally refers to a simultaneous or substantially simultaneous occurrence of a first event or action with respect to an occurrence of a second event or action. A real-time action or event may be performed within a response time of less than one or more of the following: ten seconds, five seconds, one second, a tenth of a second, a hundredth of a second, a millisecond, or less relative to at least another event or action. A real-time action may be performed by one or more computer processors.

Whenever the term "at least," "greater than" or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

In an aspect, the present disclosure provides methods and systems for processing laser speckle images. In some embodiments, a series of frames F_1, F_2, . . . , F_N of a scene illuminated with laser light may be collected using a camera. The camera may include, for example, a universal serial bus (USB) camera that uses USB technology to transfer data. The coherence of the laser light causes a speckle pattern to appear on the scene. This speckle pattern may depend on the location of the observer and the intrinsic parameters of the camera. For example, two cameras at different locations may capture different speckle patterns, and two users observing the scene (camera to eye) may not agree on the location of speckles. If the object being imaged happens to be moving, then the speckle pattern on its surface may change from frame to frame, in a random "twinkling" which does not resemble a pattern flowing with the motion of the object and may not readily be "tracked." By examining groups of neighboring pixels (either in space, or from frame to frame) and computing the mean (mu) and variance (sigma^2) of those neighboring pixels, the velocity of the object being imaged at each pixel can be computed as approximately sigma^2/mu^2. Detected motion can be due to physical motion of the object or due to blood flow in the underlying tissue. During the imaging, it is preferable to keep all non-blood flow sources of motion to a minimum.

The present disclosure provides methods and systems for computing the statistics that are used in speckle contrast maps, based at least in part on structured summation (i.e. integration). The present disclosure provides modified infinite sum algorithms in time and space. In an aspect, the present disclosure provides infinite impulse laser speckle contrast imaging (LSCI) and infinite impulse laser speckle contrast analysis (LASCA) algorithms for laser speckle contrast image processing.

The present disclosure also provides methods and systems for weighted integration of speckle signals through time and space, i.e. Gaussian LASCA. The present disclosure provides methods and systems for generating and processing pulse maps. The present disclosure provides methods and systems for infinite impulse filtering in time and space.

Conventional finite sum methods may estimate mu and sigma with sums around each pixel in space and through time. Each term in these sums may be treated identically, which introduces artifacts in the images. In contrast, the methods and systems disclosed herein can provide cleaner images by filtering the statistics using weighted sums during summation and division. Accordingly, the methods and systems disclosed herein can provide improved performance over finite sum methods that first compute a ratio of statistics and then filter.

The methods and systems disclosed herein may be implemented by deriving a statistical quantity (mu^2/sigma^2) of each pixel. These quantities may be estimated empirically.

For example, instead of estimating mu~\sum p_i over frames {i=1, ..., n}, mu in the present disclosure can be estimated by mu_t=(1−alpha)*p_t+alpha*m_(t−1). Similarly, a sum of squares xi_t=(1−alpha)*(p_t)^2+alpha*xi_(t−1) can be estimated. Mu_t and xi_t may correspond to the "counts" at time t. Sigma_t^2=xi_t−(mu_t)^2. Consequently, mu^2/sigma^2 can be simplified into an expression that uses fewer division operations, thereby optimizing computational performance.

The present disclosure provides methods and systems for optimizing and performing infinite impulse speckle temporal integration based on a running average (with alpha).

The present disclosure also provides methods and systems for optimizing and simplifying the derivation and/or computation of mu^2/sigma^2 once the "counts" have been computed.

The "counts" can be computed by iterating a weighted average through space instead of time. The methods and systems disclosed herein may be implemented using the following expression:

$$A\_11,t=(1/9)*[alpha*A\_(11,t-1)+(1-alpha)(A\_(00,t-1)+A\_(10,t-1)+A\_(20,t-1)+A\_(01,t-1)+A\_(21,t-1)+A\_(02,t-1)+A\_(12,t-1)+A\_(22,t-1))]$$

Performing this sum at each pixel may cause each pixel to become an average of itself and its neighbors. Performing the sum a second time can cause each pixel to also be an average of the neighbors of its neighbors. Iterating the sum models can include a heat diffusion process whose eigenfunctions are Gaussians, meaning that in the limit this process is equivalent to Gaussian kernel summation.

These techniques can be combined to sum through space and time simultaneously, causing each pixel to compute counts using its own and its neighbors' histories, and weighted according to proximity.

The present disclosure also provides methods and systems for weighted integration against a reference signal in time and frequency domains. In some cases, the methods and systems disclosed herein may comprise one or more aspects of kernel integration. The speckle reference signal $L^P$ measurement can be used for the purpose of a touch sensor. The speckle reference signal $L^P$ measurement may be used to generate a pulsality map or a pulse map. $L^P$ may correspond to a Lebesgue space. $L^P$ may comprise one or more spaces of integrable functions together with norms and inner products used to measure and compare those functions. $L^P$ may comprise function spaces defined using a natural generalization of the p-norm for finite-dimensional vector spaces. For instance, $L^2$ may comprise the space of square integrable functions together with the usual Euclidean Norm, and the inner product may correspond to the infinite dimensional analogue of the typical dot product of vectors. In some embodiments, $L^P$ may be correlated with an l' space in cases where the p-norm can be extended to vectors that have an infinite number of components. In some cases, l' may be used to implement one or more aspects of the present disclosure.

In a finite impulse method, flow signal may be recorded over a finite number of frames and compared to a reference signal. This comparison can be performed by dot product, normalized cross correlation, weighted measure integration, or any other similar signal/time series comparator. This comparison can occur over the entire image (full field) or over a region of interest.

The infinite impulse methods disclosed herein may use exponential moving averages to compute the integral online, frame by frame, and weighted more towards the recent past. This may save time and memory space during computation.

The pulse of a patient may modulate the flow of blood and perfusion of tissue in a periodic way. This pulse can be detected from a whole image, and used directly or used as the basis to synthesize a pure reference pulse signal of the appropriate frequency and phase. Flow which varies with the pulse signal may arise due to blood flow, while flow which does not vary with the signal may arise due to physical motion e.g. peristalsis, respiration, or camera motion. Tissue is viable if it has a detectable pulse, and if it is proximal to and attached in a non-obstructive manner to tissue with a detectable pulse. Thus pulse referencing disclosed herein can effectively filter out "false positive flow" due to certain factors.

In an aspect, the present disclosure also provides methods and systems for contact sensing based on synthetic reference signals. Two motors may spin at different rates (e.g., 200 Hz and 212 Hz) and heterodyne interference creates 12 Hz envelopes around ~200 Hz vibration. The motors may be housed in a transducer attached to a surgical tool. If the tool is in contact with the tissue, the vibrations may be transmitted into the tissue and may modulate the observed (computed) speckle contrast signal. This modulation can be detected through reference signal comparison in the frequency domain. The degree of fit to the reference signal increases with tool pressure on tissue, and as such a relative "force on tissue" can be computed. This "force on tissue" can be used for determining tool-tissue contact. An example use may be in "thread tensioning" during robotic surgery.

In an aspect, the present disclosure also provides methods and systems for simultaneous multi-band speckle imaging. The Hb and HbO2 absorption spectra intersect at points known as isosbestic points. There is such a point near 808 nm. Speckle imaging at such a point would be theoretically agnostic to oxygenation and therefore should respond on the basis of flow alone. Thus, small veins and arteries of similar size and flow should appear the same (since structurally these vesicles are more similar than larger such vessels), and un-perfused tissue will not be biased by remaining levels of oxygen, which will change over time. By simultaneously illuminating in 785 nm and 852 nm with carefully chosen intensity ratios, a scene can be imaged while maintaining invariance across Hb and HbO2. This can provide the benefit of imaging under an isosbestic point even though an optical system may not support a particular wavelength due to the need to block that wavelength which may be used for ICG excitation.

In an aspect, the present disclosure also provides methods and systems for laser speckle spectral deconvolution. Spectral deconvolution can be applied to the speckle maps developed under different wavelengths. This technique may be referred to herein as "hyperspeckle." The methods and systems disclosed herein may be implemented using any number of wavelengths. The methods and systems disclosed herein may be implemented using any one or more aspects of general spectroscopy. The methods and systems disclosed herein may be implemented for the purpose of Hb versus Parenchyma concentration determination. The methods and systems disclosed herein may be implemented to evaluate oxygenation/SP02 from speckle under two or more wavelengths.

In an aspect, the present disclosure also provides methods and systems for disk based optical phase modulation. This may be referred to herein as a "diskcombobulator." The methods and systems disclosed herein may implement a technique that uses a spinning disk with an array of flat acrylic transparent windows of different thicknesses which executes a phase modulation of the laser beam that is synchronized with a camera capture, which has mathematically analyzable repercussions on the speckle signal. A spinning disk with embedded glass plates, each of a different thickness, sequentially inserts the glass plates into the beam line of a collimated laser, which changes the effective path length of the beam in lock step with the frames of a camera capturing images of a scene illuminated by the (diffused) laser light. Without the phase modulation described above, any sequence of speckle images will have correlated speckle patterns which can cause bias in the computed contrast image when statistics are collected over time. In particular, LSCI will hallucinate high flow in low flow conditions because the speckle patterns are so correlated between frames that the variance estimate are biased very low. Introduction of the phase modulation described herein can allow accurate flow to be computed using time integration and can remove the "hallucinated flow" artifact on the low end.

In another aspect, the present disclosure also provides methods and systems for collecting raw laser frames in two (or more) different registered cameras, which may extend the abilities of laser speckle. First, the speckle in frames is computed independently. The midline of the vessel combined with parallax can give the depth of vessel. Once correspondence has been established, the speckle samples from all cameras can be combined in an algorithm which jointly estimates flow and depth.

In another aspect, the present disclosure also provides methods and systems for multi-sampling statistics prior to contrast computation as well the combination of contrast maps. Averaging multiple contrast images developed under different wavelengths. The methods and systems for multi-sampling may implement a "diskcombobulator" and/or a "stereo joint algorithm."

Aspects of the present disclosure provide a system comprising one or more computer processors and computer memory coupled thereto. The computer memory comprises machine executable code that, upon execution by the one or more computer processors, implements any of the methods described herein.

The present disclosure provides computer systems that are programmed to implement methods of the disclosure. The computer systems may be programmed or otherwise configured to implement one or more methods for infinite impulse laser speckle contrast imaging (LSCI) and/or one or more infinite impulse laser speckle contrast analysis (LASCA) algorithms for laser speckle contrast image processing.

Laser Speckle Signal Processing

In an aspect, the present disclosure provides a method for processing laser speckle signals. The method may comprise (a) obtaining (1) a laser speckle signal from a laser speckle pattern generated using at least one laser light source that is directed towards a tissue region of a subject and (2) a reference signal corresponding to a movement of a biological material of or within the subject's body. The method may further comprise (b) defining a function space based at least in part on a first function corresponding to at least the laser speckle signal. The method may further comprise (c) computing one or more measurements for the function space. The one or more measurements may be defined in part based on a second function corresponding to the reference signal. The method may further comprise (d) generating an output signal in part based on the one or more measurements for the function space. The method may further comprise (e) using the output signal to aid a surgical procedure on or near the tissue region of the subject.

The method may comprise (a) obtaining (1) a laser speckle signal from a laser speckle pattern generated using at least one laser light source. The at least one laser light source may be directed towards a tissue region of a subject.

The laser speckle signal may comprise a signal that is associated with a laser speckle pattern. The laser speckle pattern may comprise a pattern that is generated on a material when the material is exposed to (i.e., illuminated by) one or more laser light beams or pulses. The material may comprise a tissue region of a subject. The material may comprise a biological material. In some cases, the biological material may comprise a portion of an organ of a patient or an anatomical feature or structure within a patient's body. In some cases, the biological material may comprise a tissue or a surface of a tissue of the patient's body. The tissue may comprise epithelial tissue, connective tissue, organ tissue, and/or muscle tissue (e.g., skeletal muscle tissue, smooth muscle tissue, and/or cardiac muscle tissue).

The laser speckle pattern may be generated using at least one laser light source. The at least one laser light source may be configured to generate one or more laser light beams or pulses. The one or more laser beams or pulses may have a wavelength between about 100 nanometers (nm) and about 1 millimeter (mm). In some cases, the laser speckle pattern may be generated using a plurality of laser light sources configured to generate a plurality of laser beams or pulses having different wavelengths. The plurality of laser beams or pulses may have a wavelength between about 100 nanometers (nm) and about 1 millimeter (mm). In some cases, the at least one laser light source may comprise a coherent light source, such as a laser diode. In some cases, the at least one laser light source may be configured to generate light in a near-infrared spectrum range. The light in the near-infrared spectrum range may have a wavelength of about 980 nanometers (nm).

The speckle patterns may be produced due to an interference of light beams or light rays that is caused by a coherent light source (e.g., a laser) when illuminating a target site or target region (e.g., sample, tissue, organ in human body, etc.). When the light beams or light rays impinge the target site/region (e.g., a tissue surface), they may be scattered and/or reflected back from different portions of the target site/region or different features within the target site/region. Due to variations in a structure or a topology of the target site/region or variations in a position or a movement of one or more scattering particles (e.g., biological materials) in or near the target site/region, the light beams or light rays may travel different distances such that the scattered light beams or light rays are subjected to random variations in phase and/or amplitude. This may result in patterns of constructive and/or destructive interference, which may change over time depending on a position of different features and/or a movement of one or more scattering particles. The scattered light may produce a randomly varying intensity pattern known as a speckle pattern. If the scattering particles are moving, this may cause fluctuations in the interference, which may appear as intensity variations. The temporal and spatial statistics of such speckle patterns may provide information about a motion of one or more underlying objects, features, or biological materials being imaged.

One or more imaging devices may be used to image the speckle patterns. The one or more imaging devices may comprise a photodetector that is configured to receive scattered light that is reflected from different portions of the target site/region or different features within the target site/region. The laser speckle patterns may be obtained using one or more imaging devices. In some cases, the laser speckle patterns may be obtained over a plurality of frames as the plurality of frames are being received or processed in real time by the one or more imaging devices. The one or more imaging devices may comprise a camera, a video camera, a Red Green Blue Depth (RGB-D) camera, an infrared camera, a near infrared camera, a charge coupled device (CCD) image sensor, a complementary metal oxide semiconductor (CMOS) image sensor, a linear image sensor, an array silicon-type image sensor, and/or an InGaAs (Indium gallium arsenide) sensor. The one or more imaging devices may be configured to capture an image frame or a sequence of image frames. The image frame or the sequence of image frames may comprise one or more laser speckle patterns that are generated on a tissue surface using the at least one laser light source.

The image frame or the sequence of image frames may be provided to an image processing module. The image processing module may be configured to derive one or more laser speckle signals from the image frame or the sequence of image frames captured using the one or more imaging devices. In some cases, the image processing module may be configured to process the captured speckle images to convert the intensity of the scattered light within the image frame or the sequence of images frames into a digital signal. The digital signal may correspond to a laser speckle signal as described herein. In some cases, the digital signal may be used to generate one or more laser speckle contrast images and/or provide information about a biological process within a tissue region of the subject's body. In some cases, the biological process may comprise a movement of a biological material or a flow of a biological fluid within or near the tissue region.

The image processing module may be configured to process one or more raw speckle images comprising one or more speckle patterns to generate laser speckle contrast images. The laser speckle contrast images may comprise information on a speckle contrast associated with one or more features of the laser speckle patterns within the raw speckle images. The speckle contrast may comprise a measure of local spatial contrast values associated with the speckle patterns. The speckle contrast may be a function of a ratio between the standard deviation of the intensity of the scattered light and the mean of the intensity of the scattered light. If there is a lot of movement in the speckle pattern, blurring of the speckles in the speckle pattern may increase, and the standard deviation of the intensity may decrease. Consequently, the speckle contrast may be lower.

One or more laser speckle contrast images may be computed directly from a sequence of raw speckle images or image stream using one or more laser speckle contrast imaging (LSCI) and laser speckle contrast analysis (LASCA) algorithms. In some cases, the one or more laser speckle contrast imaging (LSCI) and laser speckle contrast analysis (LASCA) algorithms may comprise an infinite impulse integration algorithm. The infinite impulse integration algorithm may be configured to utilize infinite impulse integration or an exponential moving average (EMA) filter to process one or more raw laser speckle images comprising one or more laser speckle patterns. Unlike conventional methods where finite sums are computed for the contrast value, utilizing a recursive filter (e.g., EMA) may beneficially reduce the computational overhead and achieve or enable real-time imaging. The exponential moving average filter may be a weighted combination of the previous estimate (output) with the newest input data, with the sum of the weights equal to 1 so that the output matches the input at steady state. The infinite impulse integration algorithm may beneficially allow the computation of temporal and/or spatial statistics using a recursive implementation that minimizes computationally-intensive division operations. The infinite impulse integration algorithm may be configured to utilize infinite impulse integration in a spatial domain, a temporal domain, and/or a spatial-temporal domain. The infinite impulse integration algorithm may require fewer computational resources, and may require less memory for storing image frames compared to conventional LSCI or LASCA algorithms.

In some cases, the laser speckles images, the laser speckle patterns, and/or the laser speckle contrast images may be processed to obtain fluid flow information for one or more fluids that are moving and/or present in or near the tissue region. In some embodiments, the fluid may comprise blood, sweat, semen, saliva, pus, urine, air, mucus, milk, bile, a hormone, and/or any combination thereof. In some embodiments, a fluid flow rate within the target tissue may be determined by a contrast map or contrast image generated using the captured speckle images and/or one or more laser speckle signals derived from the captured speckle images.

In some cases, the method may comprise (a) obtaining (2) a reference signal corresponding to a movement of a biological material of or within the subject's body. The reference signal may comprise one or more signals that correspond to a movement of a biological material of or within the subject's body. The movement may comprise a change in a position, velocity, and/or acceleration of a biological material of or within the subject's body. In some cases, the movement may comprise a change in a position of one or more portions of a tissue region over time.

The biological material may be within the subject's body. In some cases, the biological material may be a part of the subject's body. In some cases, the biological material may comprise a tissue. The tissue may comprise epithelial tissue, connective tissue, organ tissue, and/or muscle tissue (e.g., skeletal muscle tissue, smooth muscle tissue, and/or cardiac muscle tissue). In some cases, the biological material may comprise the subject's skin. In some cases, the biological material may comprise a fluid. The fluid may comprise blood, lymph, tissue fluid, milk, saliva, semen, bile, an intracellular fluid, an extracellular fluid, an intravascular fluid, an interstitial fluid, a lymphatic fluid, and/or a transcellular fluid.

In some cases, the reference signal may correspond to a pulse of a subject. In such cases, the reference signal may be obtained or generated using a pulse signal associated with a pulse of the subject. In some cases, the pulse signal may be obtained using an external device. In some cases, the external device may comprise a pulse oximeter. In some embodiments, the method may further comprise using the pulse signal to determine if one or more features of the laser speckle pattern are attributable to a fluid flow or a physical motion that is not associated with the fluid flow.

In other cases, the reference signal may correspond to a movement of a tissue region of the subject's body. The movement may be induced by a vibration of a surgical tool that is in contact with the tissue region or another portion of the subject's body (e.g., another tissue region) that is proximal or adjacent to the tissue region. In some cases, the reference signal may be obtained or generated using a plurality of waveforms associated with vibrations induced by two or more motors that are configured to spin at different frequencies. In some cases, the two or more motors may be housed in a transducer that is coupled to a surgical tool used to perform one or more steps of a surgical procedure. The plurality of waveforms may comprise a superposition of a first waveform with a first frequency and a second waveform with a second frequency that is different from the first frequency. The first waveform may be generated by a vibration associated with a first motor spinning at a first frequency. The second waveform may be generated by a vibration associated with a second motor spinning at a second frequency. In some cases, the first waveform may comprise a carrier wave. The carrier wave may have a fixed or constant waveform. Alternatively, the carrier wave may have a variable waveform.

In some cases, the superposition of the first waveform and the second waveform may generate a pulsing waveform. The pulsing waveform may comprise a waveform that is generated from a superposition of two waveforms (i.e., the first waveform and the second waveform), which may result in a third waveform according to heterodyne interference. The third waveform may comprise an interference waveform that is modulated on and off in wave packets. The interference effect between the two constant waveforms may cause the pulsing waveform. Each of the two or more motors may produce a single constant waveform, and the pulsing may arise in the biological material that the two or more motors are transducing.

The method may further comprise (b) defining a function space based at least in part on a first function corresponding to at least the laser speckle signal. The function space may comprise a topological vector space whose points are functions. In some cases, the function space may be a Banach space. A Banach space may comprise a complete normed vector space. The Banach space may comprise a vector space with a metric that allows for a computation of vector lengths and distances between vectors and that is complete in the sense that a Cauchy sequence of vectors always converges to a well-defined limit that is within the space. In some cases, the function space may be a Hilbert space. A Hilbert space may be a Banach space whose norm is determined by an inner product. In some cases, the function space may be a Lebesgue space or an $L^P$ space. The $L^P$ space may comprise a space of measurable functions for which the p-th power of the absolute value of each function is Lebesgue integrable. The $L^P$ space may comprise one or more spaces of integrable functions together with norms and inner products usable to measure and compare those functions. The $L^P$ space may comprise a function space defined using a natural generalization of the p-norm for infinite dimensional vector spaces. In some cases, the $L^P$ space may be correlated with an $l^P$ space in cases where the p-norm can be extended to vectors that have an infinite number of components. The systems and methods disclosed herein may be implemented using an $L^P$ space and/or an $l^P$ space.

In some cases, the function space may be defined based at least in part on a first function corresponding to at least the laser speckle signal. In some cases, the first function may comprise an infinite dimensional vector function. The infinite dimensional vector function may comprise a set of output values lying in an infinite dimensional vector space. In some cases, the function space may correspond to a set of functions associated with a set of laser speckle signals. The set of functions may comprise one or more infinite dimensional vector functions. The set of laser speckle signals may comprise one or more laser speckle signals generated using the at least one laser light source. The set of laser speckle signal may comprise one or more possible laser speckle signals generated using one or more laser light sources.

The method may further comprise (c) computing one or more measurements for the function space. The one or more measurements may be defined in part based on a second function corresponding to a reference signal. As described above, the reference signal may be associated with a pulse of a subject, or a vibration of a plurality of motors that are coupled to a surgical instrument or tool in contact with a tissue region of a subject. In some cases, the second function may comprise an infinite dimensional vector function. The infinite dimensional vector function may comprise a set of output values lying in an infinite dimensional vector space.

In some cases, the one or more measurements for the function space may be derived in part by comparing the first function and the second function. Comparing the first function and the second function may comprise projecting the laser speckle signal onto the reference signal, or projecting the reference signal onto the laser speckle signal, to compare a first set of pixel values associated with the laser speckle signal against a second set of pixel values associated with the reference signal. In some cases, comparing the first function and the second function may comprise computing at least one of an inner product, a dot product, a cross-correlation, an auto-correlation, a normalized cross-correlation, or a weighted measure integration using the first function and the second function. In some cases, comparing the first function and the second function may comprise using one or more signal or time series comparators to determine an amount or degree of correlation between the first function and the second function.

In some cases, the comparison of the first function and the second function may be performed in a time domain and/or a frequency domain. In some cases, the comparison of the first function and the second function may occur over at least a portion of a laser speckle image comprising the laser speckle pattern. In some cases, the portion of the laser speckle image may correspond to one or more regions of interest in or near the tissue region of the subject. In some cases, the comparison of the first function and the second function may be performed substantially in real time and frame by frame for each new image frame obtained for a laser speckle pattern.

In some cases, the laser speckle signal may comprise a modulated laser speckle signal that is generated when a surgical tool is placed in contact with a tissue region of the subject. The surgical tool may comprise or be coupled to two or more motors that may vibrate. In such cases, the one or more measurements for the function space may correspond to an amount or a degree of correlation between the modulated laser speckle signal and the plurality of waveforms associated with vibrations induced by two or more motors spinning at different frequencies, in a time domain and/or a frequency domain.

In some cases, the method may further comprise (d) generating an output signal in part based on the one or more measurements for the function space.

As described above, in some cases the reference signal may be obtained or generated using a pulse signal associated with a pulse of the subject. In such cases, the one or more measurements for the function space may correspond to an amount or a degree of correlation between the laser speckle signal and the pulse signal. In such cases, the output signal may comprise a flow signal that is usable to generate a perfusion flow map. A perfusion flow map may comprise a visualization of a flow of a biological material through one or more regions (e.g., one or more tissue regions) of the subject's body. In some cases, the flow signal may be usable to eliminate one or more false positives in the perfusion flow map. The one or more false positives may correspond to one or more areas in the perfusion flow map that indicate a movement of a fluid even if there is no fluid actually flowing through the one or more areas. In some cases, the pulse signal and/or the flow signal derived using the pulse signal may be used to determine if one or more features of a laser speckle pattern are attributable to a fluid flow or an external physical motion that is not necessarily attributable to a fluid flow.

As described above, in some cases the reference signal may be obtained or generated using a plurality of waveforms associated with vibrations induced by two or more motors that are configured to spin at different frequencies. The two or more motors may be housed in a transducer that is coupled to a surgical tool. In such cases, the one or more measurements for the function space may correspond to an amount or a degree of correlation between the laser speckle signal and the plurality of waveforms associated with vibrations induced by the two or more motors. In such cases, the output signal may comprise a flow signal that is usable to generate a perfusion flow map and to determine if one or more features of the perfusion flow map are attributable to a fluid flow or an external physical motion that is not necessarily attributable to a fluid flow. Alternatively, the output signal may comprise a force signal that is usable to determine if the surgical tool is touching the tissue region of the subject. In some cases, the output signal may comprise a force signal that is usable to determine an amount of force exerted on a tissue in or near the tissue region of the subject by the surgical tool when the surgical tool is placed in contact with the tissue region of the subject. In other cases, the output signal may comprise a force signal that is usable to determine an amount of tension in a thread that is being handled by a surgeon or a robotic suturing device. The robotic suturing device may be autonomous or semi-autonomous.

In some cases, the laser speckle signal may comprise a modulated laser speckle signal that is generated when the surgical tool is placed in contact with the tissue region of the subject. In such cases, the one or more measurements for the function space may correspond to an amount or degree of correlation between the modulated laser speckle signal and the reference signal associated with the plurality of waveforms generated by the vibrations induced by the two or more motors, in a time domain and/or a frequency domain. In such cases, the output signal may comprise a flow signal that is usable to generate a perfusion flow map and to determine if one or more features of the perfusion flow map are attributable to a fluid flow or an external physical motion that is not necessarily attributable to a fluid flow. Alternatively, the output signal may comprise a force signal that is usable to determine if the surgical tool is touching the tissue region of the subject. In some cases, the output signal may comprise a force signal that is usable to determine an amount of force exerted on a tissue in or near the tissue region of the subject by the surgical tool when the surgical tool is placed in contact with the tissue region of the subject. In other cases, the output signal may comprise a force signal that is usable to determine an amount of tension in a thread that is being handled by a surgeon or a robotic suturing device.

The method may further comprise (e) using the output signal to aid a surgical procedure on or near the tissue region of the subject. The surgical procedure may comprise one or more surgical procedures that may be performed using one or more medical tools or instruments. The one or more medical tools or instruments may comprise an endoscope or a laparoscope. In some cases, the one or more surgical procedures may be performed using one or more robotic devices. The one or more robotic devices may be configured for autonomous and/or semi-autonomous surgery. In some cases, the surgical procedure may comprise one or more general surgical procedures, neurosurgical procedures, orthopedic procedures, and/or spinal procedures. In some cases, the one or more surgical procedures may comprise colectomy, cholecystectomy, appendectomy, hysterectomy, thyroidectomy, and/or gastrectomy. In some cases, the one or more surgical procedures may comprise hernia repair, and/or one or more suturing operations. In some cases, the one or more surgical procedures may comprise bariatric surgery, large or small intestine surgery, colon surgery, hemorrhoid surgery, and/or biopsy (e.g., liver biopsy, breast biopsy, tumor or cancer biopsy, etc.).

The output signal may be used to aid a surgical procedure. In some cases, the output signal may comprise a flow signal that may be used to generate a perfusion flow map. The flow signal may be used to help a surgical operator visualize a flow of a biological material through one or more regions (e.g., one or more tissue regions) of a subject's body. The flow signal may also be used to eliminate one or more false positives in the perfusion flow map. The one or more false positives may correspond to one or more areas in the perfusion flow map that indicate a movement of a fluid even if there is no fluid actually flowing through the one or more areas. In other cases, the output signal may comprise a force signal that may be used to determine if a surgical tool is touching a tissue region of the subject. The force signal may be used by a surgical operator to determine an amount of force exerted on a tissue in or near the tissue region of the subject by the surgical tool when the surgical tool is placed in contact with the tissue region of the subject. In some cases, the force signal may be used to determine an amount of tension in a thread that is being handled by a surgeon or a robotic suturing device. The robotic suturing device may be autonomous or semi-autonomous.

In another aspect, the present disclosure provides a method for generating a perfusion flow map. The method may comprise: (a) obtaining a laser speckle signal from a laser speckle pattern generated using at least one laser light source that is directed towards a tissue region of a subject; (b) generating a reference signal from a pulse signal associated with a pulse of the subject; (c) comparing the laser speckle signal to the reference signal; and (d) generating the perfusion flow map based in part on the comparison of the laser speckle signal to the reference signal.

In some cases, the laser speckle signal may be obtained over a plurality of frames as the plurality of frames are being received or processed in real time. In some cases, the laser speckle pattern may be generated using a plurality of laser light sources configured to generate a plurality of laser beams or pulses having different wavelengths or frequencies. The plurality of laser beams or pulses may have a wavelength between about 100 nanometers (nm) and about 1 millimeter (mm).

In some cases, comparing the laser speckle signal to the reference signal may comprise defining a function space based at least in part on a first function corresponding to at least the laser speckle signal. The function space may comprise a Lebesgue function space. In some cases, the first function may comprise an infinite dimensional vector function with a set of output values lying in an infinite dimensional vector space.

In some cases, the function space may correspond to a set of functions associated with a set of laser speckle signals generated using the at least one laser light source. The set of functions may comprise one or more infinite dimensional vector functions with a set of output values lying in an infinite dimensional vector space. The set of laser speckle signals may comprise one or more laser speckle signals that are generated using one or more laser light sources.

In some cases, comparing the laser speckle signal to the reference signal may comprise computing one or more measurements for the function space. The one or more measurements may be defined in part based on a second function corresponding to the reference signal. The second function may comprise an infinite dimensional vector function with a set of output values lying in an infinite dimensional vector space. The one or more measurements may be used to generate the perfusion flow map. The one or more measurements for the function space may correspond to an amount or degree of correlation between the laser speckle signal and the pulse signal.

In some cases, the one or more measurements for the function space may be derived in part by comparing the first function and the second function. In some cases, comparing the first function and the second function may comprise computing at least one of an inner product, a dot product, a cross-correlation, an auto-correlation, a normalized cross-correlation, or a weighted measure integration using the first function and the second function. In some cases, comparing the first function and the second function may comprise using one or more signal or time series comparators to determine an amount or degree of correlation between the first function and the second function. In some cases, the one or more measurements for the function space may be derived in part by comparing the laser speckle signal and the reference signal. Comparing the laser speckle signal and the reference signal may comprise projecting the laser speckle signal onto the reference signal, or projecting the reference signal onto the laser speckle signal, to compare a first set of pixel values associated with the laser speckle signal against a second set of pixel values associated with the reference signal.

In some cases, the comparison of the first function and the second function may be performed in a time domain and/or a frequency domain. In some cases, the comparison of the first function and the second function may occur over at least a portion of a laser speckle image, the portion comprising one or more regions of interest in the laser speckle image. In some cases, the comparison of the first function and the second function may be performed substantially in real time and frame by frame for each new image frame captured for a laser speckle pattern.

In some embodiments, the method may further comprise using the comparison of the laser speckle signal to the reference signal to determine if one or more features of the laser speckle pattern are attributable to a fluid flow or a physical motion. In some embodiments, the method may further comprise using the comparison of the laser speckle signal to the reference signal to eliminate one or more false positives in the perfusion flow map. The one or more false positives may correspond to one or more areas in the perfusion flow map that indicate a movement but do not have fluid flowing through the one or more areas.

In some embodiments, the method may further comprise using the perfusion flow map to determine if the tissue region comprises viable tissue that receives or is capable of receiving blood flow. In some embodiments, the method may further comprise using the perfusion flow map to detect one or more critical structures that are not visible using conventional imaging techniques.

In another aspect, the present disclosure provides a method for determining a force exerted on a tissue that is in or near a tissue region of a subject. The method may comprise: (a) obtaining a laser speckle signal from a laser speckle pattern generated using at least one laser light source that is directed towards the tissue region of the subject; (b) generating a reference signal using a plurality of waveforms associated with vibrations of two or more motors that are configured to spin at different frequencies; (c) modulating the laser speckle signal using the reference signal; (d) comparing the modulated laser speckle signal to the reference signal; and (e) generating a force signal based in part on the comparison of the modulated laser speckle signal to the reference signal.

The laser speckle signal may be obtained from a laser speckle pattern generated using at least one laser light source that is directed towards the tissue region of the subject. In some cases, the laser speckle pattern may be generated using a plurality of laser light sources configured to generate a plurality of laser beams or pulses having different wavelengths or frequencies. The plurality of laser beams or pulses may have a wavelength between about 100 nanometers (nm) and about 1 millimeter (mm). In some cases, the laser speckle signal may be obtained over a plurality of image frames as the plurality of image frames are being received or processed in real time.

The reference signal may be generated using a plurality of waveforms associated with vibrations of two or more motors that are configured to spin at different frequencies. The two or more motors may be housed in a transducer that is coupled to a surgical tool that is used to perform one or more steps of a surgical procedure. The plurality of waveforms may comprise a superposition of a first waveform with a first frequency and a second waveform with a second frequency that is different from the first frequency. The first waveform may be associated with a first motor of the two or more motors. The second waveform may be associated with a second motor of the two or more motors. The superposition of the first waveform and the second waveform may generate a pulsing waveform. The first waveform may comprise a carrier waveform. In some cases, the carrier wave may have a fixed or constant waveform. In some cases, the carrier wave may have a variable waveform.

The reference signal may be generated when the surgical tool is placed in contact with a portion of the subject's body. The portion of the subject's body may comprise a tissue region of the subject's body. The reference signal may be generated based on a vibration induced at a first tissue region that is remote from a second tissue region where the laser light source is directed to generate the laser speckle pattern, or where a surgical procedure is being performed. The first tissue region and the second tissue region may be adjacent to each other.

In some cases, the surgical tool may be used to modulate the laser speckle signal. The modulated laser speckle signal may be generated when the surgical tool is placed in contact with the tissue region of the subject. The vibrations induced by the two or more motors coupled to the surgical tool may modulate the laser speckle pattern generated on a tissue region of the subject using the laser light source.

A force signal may be generated based in part on a comparison of the modulated laser speckle signal to the reference signal. Comparing the modulated laser speckle signal and the reference signal may comprise projecting the modulated laser speckle signal onto the reference signal, or projecting the reference signal onto the modulated laser speckle signal, to compare a first set of pixel values associated with the modulated laser speckle signal against a second set of pixel values associated with the reference signal. In some cases, comparing the modulated laser speckle signal to the reference signal may comprise (i) defining a function space based at least in part on a first function corresponding to at least the modulated laser speckle signal, and (ii) computing one or more measurements for the function space. The one or more measurements may be defined in part based on a second function corresponding to the reference signal. The one or more measurements may be used to generate the force signal. In some cases, the one or more measurements for the function space may correspond to an amount or degree of correlation between the modulated laser speckle signal and the reference signal in a time domain or a frequency domain.

In some cases, the one or more measurements for the function space may be derived in part by comparing the first function and the second function. In some cases, comparing the first function and the second function may comprise computing at least one of an inner product, a dot product, a cross-correlation, an auto-correlation, a normalized cross-correlation, or a weighted measure integration using the first function and the second function. In some cases, comparing the first function and the second function may comprise using one or more signal or time series comparators to determine an amount or degree of correlation between the first function and the second function. The comparison of the first function and the second function may be performed in a time domain or a frequency domain. In some cases, the comparison of the first function and the second function may occur over at least a portion of a laser speckle image comprising the laser speckle pattern. The portion may correspond to one or more regions of interest in or near the tissue region of the subject. In some cases, the comparison of the first function and the second function may be performed substantially in real time and frame by frame for each new image frame captured for a laser speckle pattern.

In some cases, the function space may comprise a Lebesgue function space. The function space may correspond to a set of functions associated with a set of laser speckle signals generated using the at least one laser light source. In some cases, the set of laser speckle signals may comprise the modulated laser speckle signal. In some cases, the set of functions may comprise one or more infinite dimensional vector functions comprising a set of output values lying in an infinite dimensional vector space.

As described above, the one or more measurements for the function space may be used to generate a force signal. The force signal may be used to determine if the surgical tool is touching a tissue that is in or near the tissue region of the subject. The force signal may be used to determine an amount of force exerted on a tissue that is in or near the tissue region of a subject by the surgical tool when the surgical tool is placed in contact with the tissue region of the subject. The force signal may be used to determine an amount of tension in a thread that is being handled by a surgeon or a robotic suturing device.

In another aspect, the present disclosure provides systems that may be configured to implement any of the methods disclosed herein. FIG. 1 illustrates an exemplary system for processing laser speckle signals. The system may comprise an image acquisition module 10 that is configured to capture one or more images of a surgical scene. The one or more images may comprise RGB images and/or laser speckle images. The image acquisition module 10 may be configured to provide the one or more images of the surgical scene to an image processing and signal analysis module 11. The image processing and signal analysis module 11 may be configured to process the one or more images of the surgical scene to generate one or more output signals 12. Processing the one or more images of the surgical scene may comprise extracting one or more laser speckle signals from the laser speckle images and comparing the one or more laser speckle signals against a reference signal to derive the one or more output signals 12. The one or more output signals 12 may comprise, for example, a perfusion flow map, a force signal, a thread tension value, and/or a needle driver pressure value.

Figure 2:
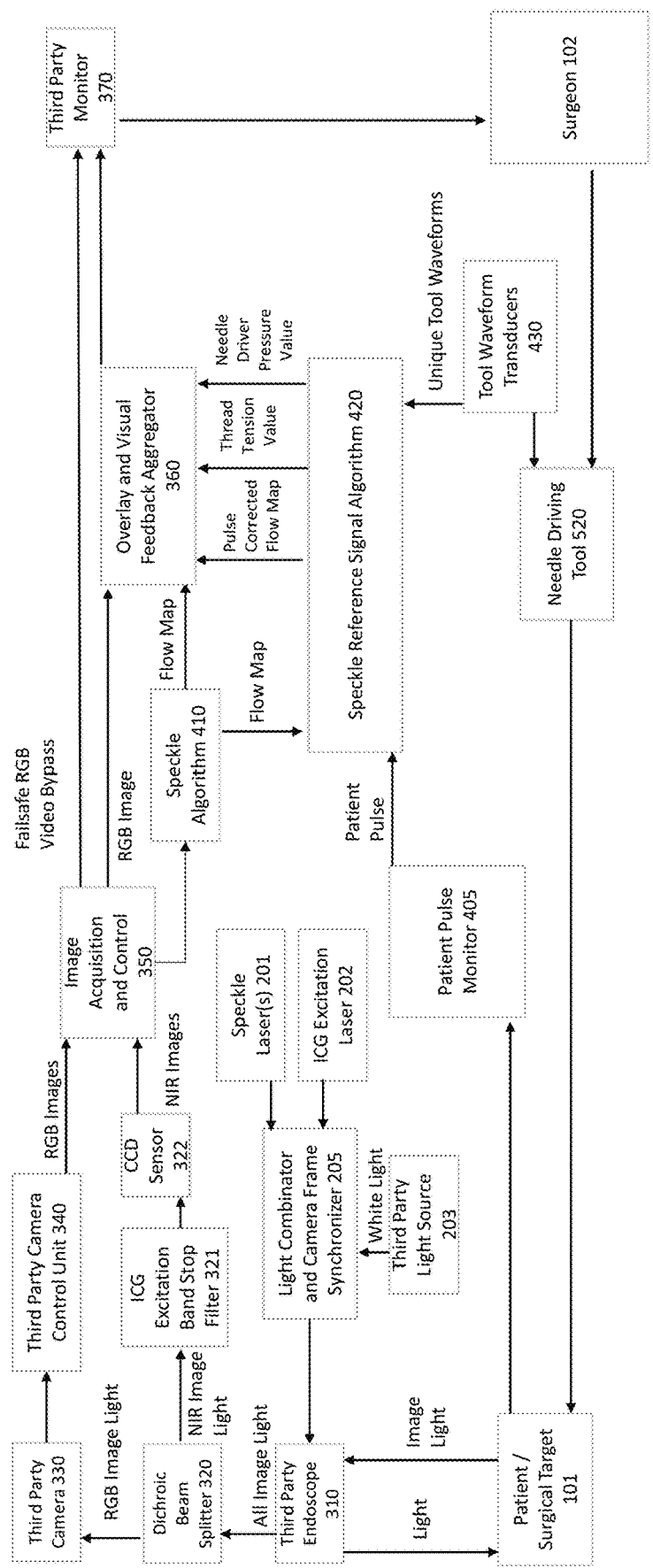
FIG. 2 schematically illustrates a system for processing laser speckles for a surgical operation, in accordance with some embodiments.
Figure 3:
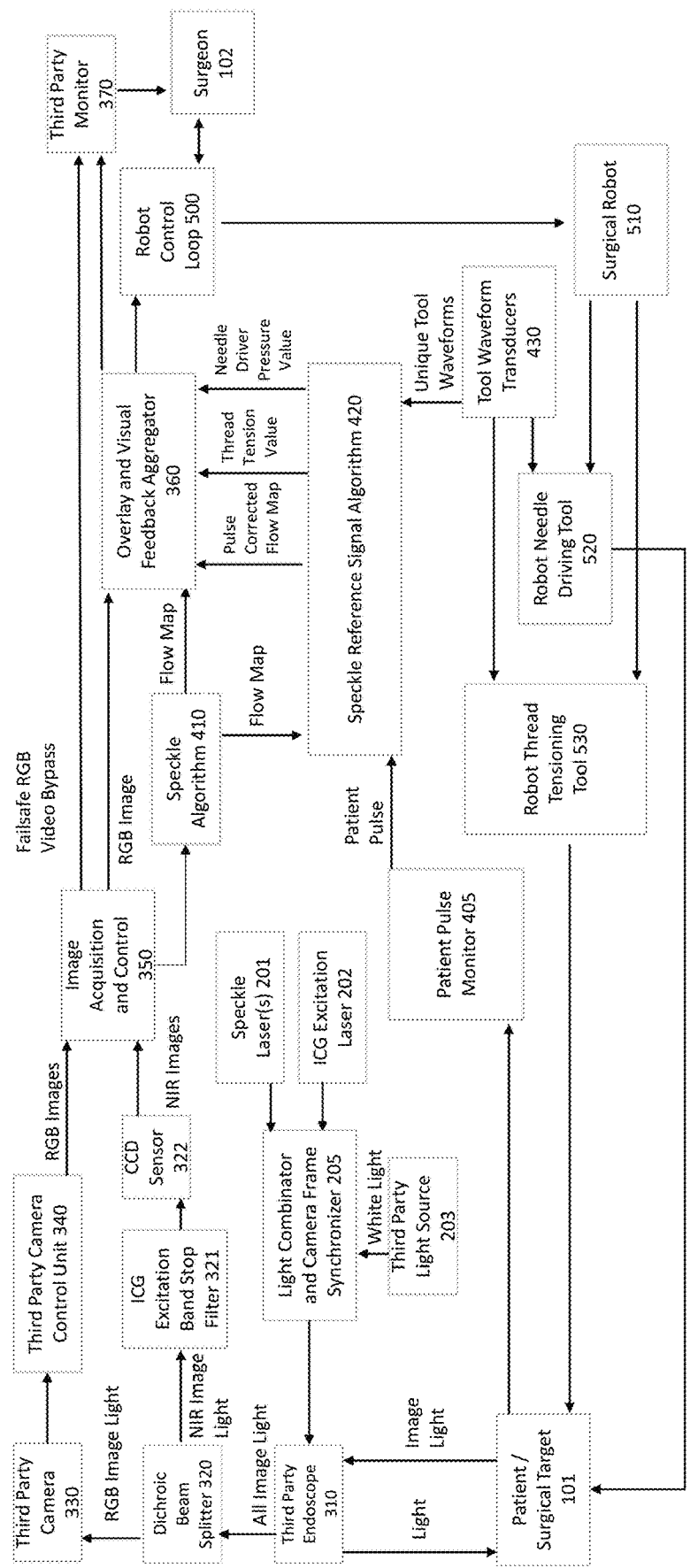
FIG. 3 schematically illustrates a system for processing laser speckles for a surgical operation comprising a surgeon supervising or operating a robot, in accordance with some embodiments.
Figure 4:
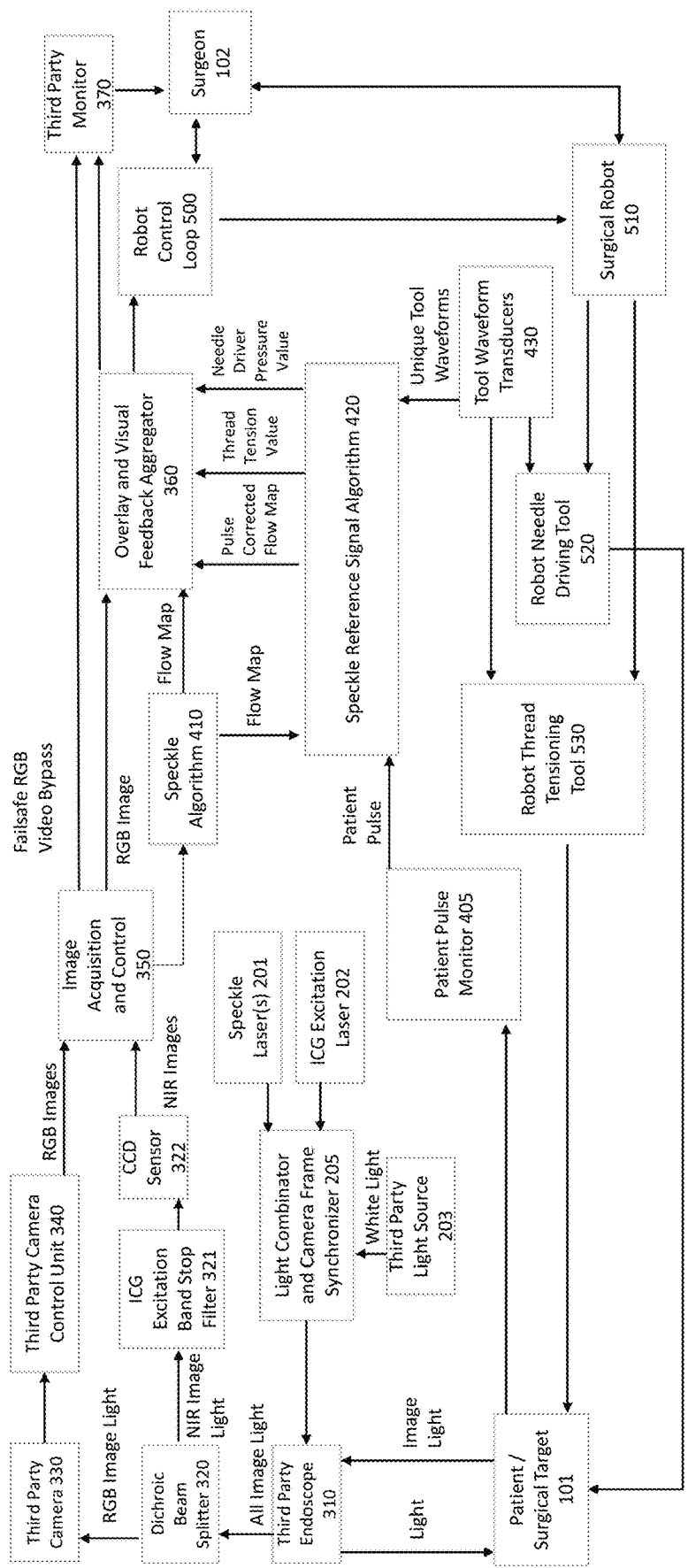
FIG. 4 schematically illustrates a system for processing laser speckles for a surgical operation comprising a surgeon working with a robot, in accordance with some embodiments.

FIG. 2, FIG. 3, and FIG. 4 illustrate systems that may be configured to process one or more laser speckle signals to aid a surgical procedure on or near a surgical target 101 of a patient. The surgical procedure may be performed by a surgeon 102. The system may be configured to compare the one or more laser speckle signals against a reference signal in order to aid a surgeon's performance of one or more steps of a surgical procedure.

The system may comprise one or more laser light sources 201 configured to generate one or more laser light beams. The one or more laser light beams may be used to generate at least one laser speckle pattern on the surgical target 101. In some cases, the system may comprise an indocyanine green (ICG) excitation light source 202 configured to generate an ICG excitation light beam. In some cases, the system may comprise a white light source 203 configured to generate one or more white light beams. The system may comprise a light combination module 205. The light combination module 205 may be configured to combine the one or more laser light beams, the ICG excitation light beam, and the one or more white light beams. In some cases, the light combination module 205 may comprise a camera frame synchronizer. The camera frame synchronizer may be configured to control an exposure of the laser sources 201, the ICG excitation light source 202, and the white light source 203 relative to a frame capture rate of a camera or imaging sensor. The light combination module 205 may be configured to generate a combined light beam comprising the one or more laser light beams, the excitation light beam, and the one or more white light beams. The combined light beam may be provided to an endoscope 310. The endoscope 310 may be configured to direct the combined light beam to the surgical target 101. The endoscope 310 may be configured to receive a reflected image light beam and to direct the reflected image light beam to a beam splitter 320. The reflected image light beam may be generated when the combined light beam is reflected off of a portion of the surgical target 101. The reflected image light beam may comprise at least a portion of the combined light beam. The beam splitter 320 may comprise a dichroic mirror. The beam splitter 320 may be configured to direct a first portion of the reflected image light beam to a camera 330 and a camera control unit 340 that is configured to process the first portion of the reflected image light beam. The first portion of the reflected image light beam may comprise at least a portion of the white light beam. The beam splitter 320 may be configured to direct a second portion of the reflected image light beam to an ICG excitation band stop filter 321 and an image sensor 322. The image sensor 322 may comprise a charge coupled device (CCD) sensor or a complementary metal oxide semiconductor (CMOS) sensor. The second portion of the reflected image light beam may comprise at least a portion of the ICG excitation light beam and/or the one or more laser light beams. The camera control unit 340 may be configured to generate one or more RGB images of the surgical target 101 using the first portion of the reflected image light beam. The image sensor 322 may be configured to generate one or more near infrared images using the second portion of the reflected image light beam. The camera control unit 340 may be configured to provide the one or more RGB images to an image acquisition unit 350. The image sensor 322 may be configured to provide the one or more near infrared images to the image acquisition unit 350. The image acquisition unit 350 may be configured to provide the one or more RGB images and/or the one or more near infrared images to a monitor 370 that is configured to display the RGB images and/or the near infrared images to the surgeon 102.

In some cases, the image acquisition unit 350 may be configured to provide the one or more RGB images and/or the one or more near infrared images to an overlay and visual feedback aggregator 360. The overlay and visual feedback aggregator 360 may be configured to generate one or more overlaid images using the one or more RGB images and/or the one or more near infrared images. The one or more overlaid images may be provided to the monitor 370 so that the surgeon 102 may view the surgical target 101.

In some cases, the overlay and visual feedback aggregator 360 may be configured to receive a flow map that is generated using a laser speckle processing module 410. The laser speckle processing module 410 may be configured to generate the flow map by processing one or more laser speckle patterns or laser speckle signals using a laser speckle algorithm. The one or more laser speckle patterns or laser speckle signals may be generated using the one or more laser light sources 201. The overlay and visual feedback aggregator 360 may be configured to overlay the flow map onto the one or more RGB images and/or the one or more near infrared images to provide an augmented flow map to the surgeon 102 via the monitor 370.

In some cases, the laser speckle processing module 410 may be configured to provide the flow map to a reference signal processing unit 420. The reference signal processing unit 420 may be configured to receive a reference pulse signal obtained using a patient pulse monitor 405. The patient pulse monitor 405 may be configured to generate the reference pulse signal based on a measurement or a detection of a pulse of the patient 101. In some cases, the patient pulse monitor may comprise a pulse oximeter. The reference signal processing unit 420 may be configured to process the reference pulse signal and the flow map to generate a pulse corrected flow map. The pulse corrected flow map may be transmitted to the overlay and visual feedback aggregator 360, which may be configured to provide the pulse corrected flow map to the monitor 370 for the surgeon 102 to view.

In some cases, the reference signal processing unit 420 may be configured to receive a tool waveform reference signal that is generated using a tool waveform transducer 430. The tool waveform transducer 430 may be configured to generate the tool waveform reference signal based at least in part on a vibration of two or more motors that are coupled to a medical tool 520. In some cases, the medical tool 520 may comprise a needle driving tool for performing a suturing operation on the surgical target 101. In some cases, the reference signal processing unit 420 may be configured to process the tool waveform reference signal to determine a thread tension value and/or a needle driver pressure value. The thread tension value and/or the needle driver pressure value may be provided to the overlay and visual feedback aggregator 360. The overlay and visual feedback aggregator 360 may be configured to display the thread tension value and/or the needle driver pressure value on or within the one or more RGB images, the one or more near infrared images, the flow map, the pulse corrected flow map, and/or any overlays comprising such images or flow maps. The thread tension value and/or the needle driver pressure value may be provided to the surgeon 102 for viewing via the monitor 370. In some cases, the thread tension value and/or the needle driver pressure value may be used by the surgeon 102 to adjust a usage, a movement, an operation, a position, and/or an orientation of the medical tool 520. In some cases, the thread tension value and/or the needle driver pressure value may be used by the surgeon 102 to adjust a pressure exerted on the surgical target 101 by the medical tool 520 during an operation of the medical tool 520.

FIG. 3 illustrates the system shown in FIG. 2 in accordance with embodiments where a surgeon 102 supervises an operation of a surgical robot 510. As shown in FIG. 3, in some cases, the tool waveform transducer 430 may be configured to generate a tool waveform reference signal based at least in part on a movement of a robot needle driving tool 520 and/or a robot thread tensioning tool 530. In some cases, the movement may comprise a movement of a tissue region that is induced by a vibration of two or more motors that are coupled to the robot needle driving tool 520 and/or the robot thread tensioning tool 530. In some cases, the reference signal processing unit 420 may be configured to process the tool waveform reference signal to determine a thread tension value and/or a needle driver pressure value associated with a usage of the robot needle driving tool 520 and/or the robot thread tensioning tool 530. In some cases, the thread tension value and/or the needle driver pressure value may be provided to a robot control loop 500 via the overlay and visual feedback aggregator 360. The robot control loop 500 may be configured to provide the thread tension value and/or the needle driver pressure value to the surgical robot 510, which may be configured to use the thread tension value and/or the needle driver pressure value to adjust a usage, a movement, an operation, a position, and/or an orientation of the robot needle driving tool 520 and/or the robot thread tensioning tool 530. In some cases, the surgical robot 510 may be configured to use the thread tension value and/or the needle driver pressure value to adjust a pressure exerted on the surgical target 101 by the robot needle driving tool 520 and/or the robot thread tensioning tool during an operation of the robot needle driving tool 520 and/or the robot thread tensioning tool.

FIG. 4 illustrates the system shown in FIG. 3 in accordance with embodiments where a surgeon 102 works collaboratively with a surgical robot 510. As shown in FIG. 4, in some cases, the surgeon 102 may use the thread tension value and/or the needle driver pressure value displayed to the surgeon 102 via the monitor 370 to adjust an operation of the surgical robot 510. Adjusting the operation of the surgical robot 510 may comprise adjusting a usage, a movement, an operation, a position, and/or an orientation of the robot needle driving tool 520 and/or the robot thread tensioning tool 530. In some cases, adjusting the operation of the surgical robot 510 may comprise adjusting a pressure exerted on the surgical target 101 by the robot needle driving tool 520 and/or the robot thread tensioning tool during an operation of the robot needle driving tool 520 and/or the robot thread tensioning tool.

Figure 5:
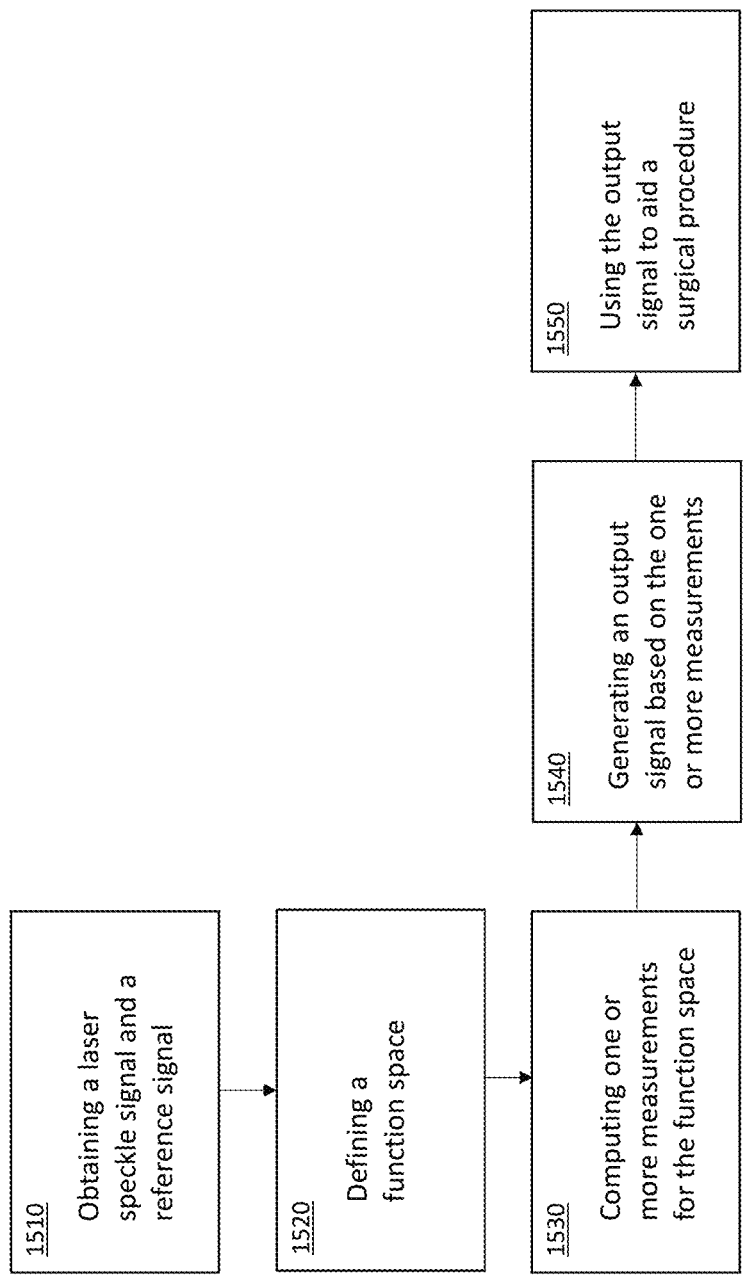
FIG. 5 schematically illustrates a method for signal processing, in accordance with some embodiments.

FIG. 5 illustrates an exemplary method for signal processing. The method may comprise a step 1510 comprising obtaining (1) a laser speckle signal from a laser speckle pattern generated using at least one laser light source that is directed towards a tissue region of a subject and (2) a reference signal corresponding to a movement of a biological material of or within the subject's body. The method may comprise another step 1520 comprising defining a function space based at least in part on a first function corresponding to at least the laser speckle signal. The method may comprise another step 1530 comprising computing one or more measurements for the function space, wherein the one or more measurements are defined in part based on a second function corresponding to the reference signal. The method may comprise another step 1540 comprising generating an output signal in part based on the one or more measurements for the function space. The method may comprise another step 1550 comprising using the output signal to aid a surgical procedure on or near the tissue region of the subject.

Figure 6:
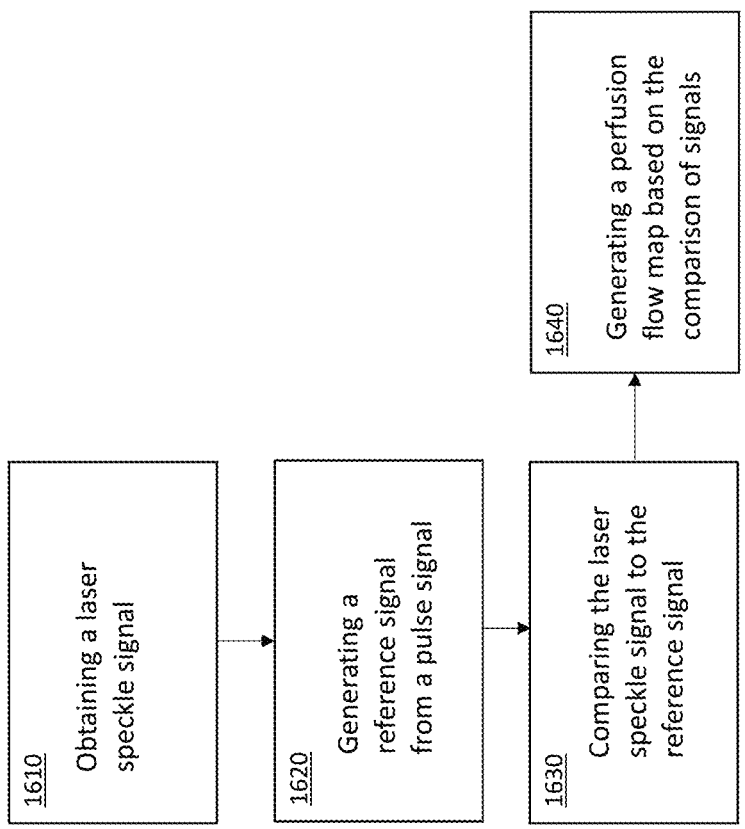
FIG. 6 schematically illustrates a method for generating a perfusion flow map, in accordance with some embodiments.

FIG. 6 illustrates an exemplary method for generating a perfusion flow map. The method may comprise a step 1610 comprising obtaining a laser speckle signal from a laser speckle pattern generated using at least one laser light source that is directed towards a tissue region of a subject. The method may comprise another step 1620 comprising generating a reference signal from a pulse signal associated with a pulse of the subject. The method may comprise another step 1630 comprising comparing the laser speckle signal to the reference signal. The method may comprise another step 1640 comprising generating the perfusion flow map based in part on the comparison of the laser speckle signal to the reference signal.

Figure 7:
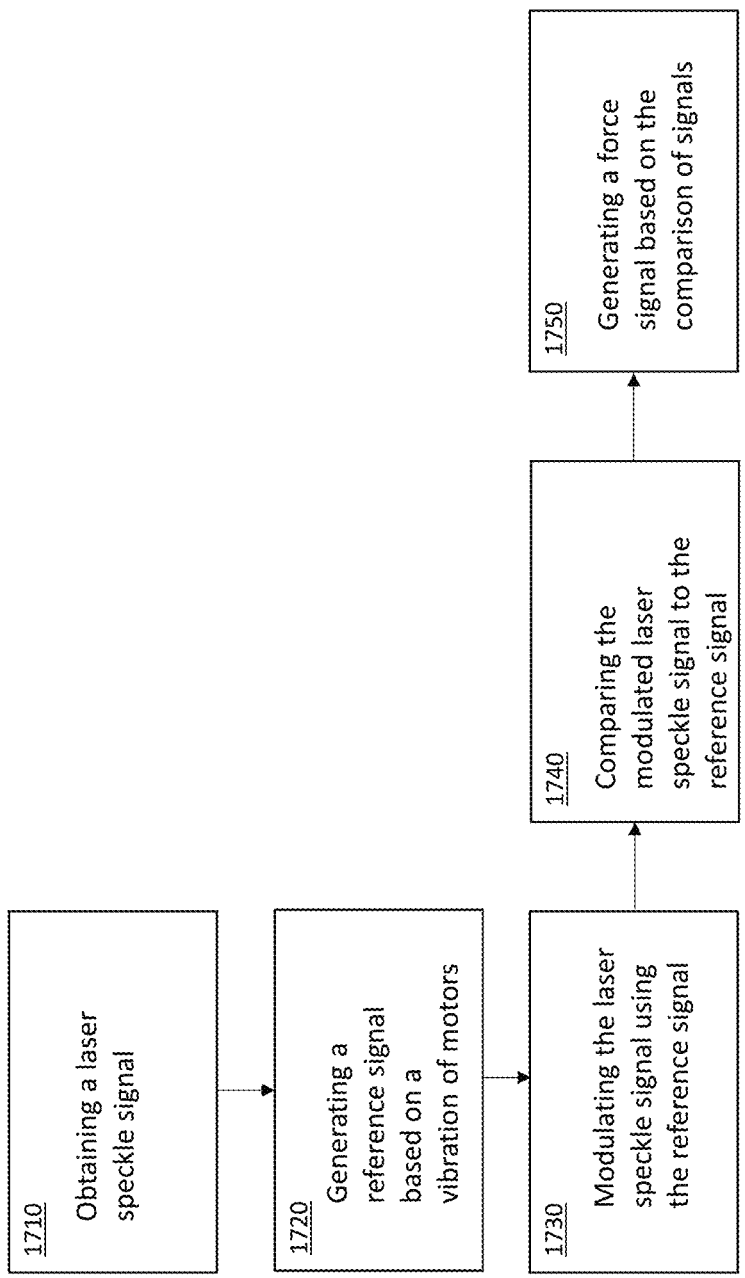
FIG. 7 schematically illustrates a method for estimating a force exerted on a tissue, in accordance with some embodiments.

FIG. 7 illustrates an exemplary method for estimating a force exerted on a tissue that is in or near a tissue region of a subject. The method may comprise a step 1710 comprising obtaining a laser speckle signal from a laser speckle pattern generated using at least one laser light source that is directed towards the tissue region of the subject. The method may comprise another step 1720 comprising generating a reference signal using a plurality of waveforms associated with vibrations of two or more motors that are configured to spin at different frequencies. The method may comprise another step 1730 comprising modulating the laser speckle signal using the reference signal. The method may comprise another step 1740 comprising comparing the modulated laser speckle signal to the reference signal. The method may comprise another step 1750 comprising generating a force signal based in part on the comparison of the modulated laser speckle signal to the reference signal.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Figure 8:
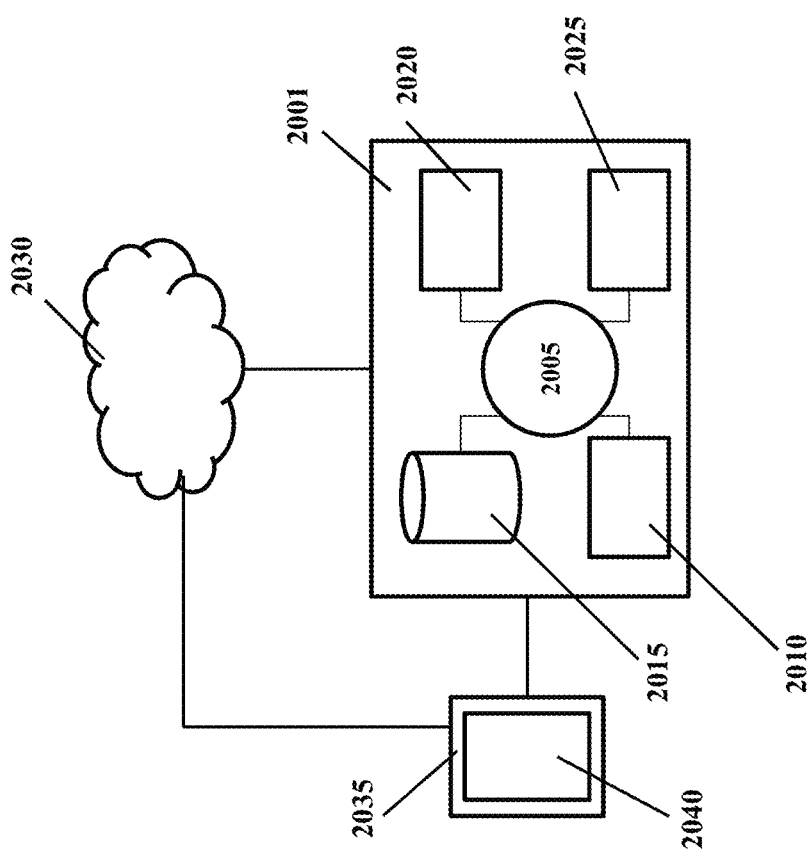
FIG. 8 schematically illustrates a computer system that is programmed or otherwise configured to implement methods provided herein.

In another aspect, the present disclosure provides computer systems that are programmed or otherwise configured to implement methods of the disclosure. FIG. 8 shows a computer system 2001 that is programmed or otherwise configured to implement a method for processing laser speckle signals. The method may comprise (a) obtaining (1) a laser speckle signal from a laser speckle pattern generated using at least one laser light source that is directed towards a tissue region of a subject and (2) a reference signal corresponding to a movement of a biological material of or within the subject's body; (b) defining a function space based at least in part on a first function corresponding to at least the laser speckle signal; (c) computing one or more measurements for the function space, wherein the one or more measurements are defined in part based on a second function corresponding to the reference signal; (d) generating an output signal in part based on the one or more measurements for the function space; and (e) using the output signal to aid a surgical procedure on or near the tissue region of the subject. The computer system 2001 can be an electronic device of a user or a computer system that is remotely located with respect to the electronic device. The electronic device can be a mobile electronic device.

The computer system 2001 may include a central processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data. The computer system 2001 can be operatively coupled to a computer network ("network") 2030 with the aid of the communication interface 2020. The network 2030 can be the Internet, an internet and/or extranet, or an intranet and/or extranet that is in communication with the Internet. The network 2030 in some cases is a telecommunication and/or data network. The network 2030 can include one or more computer servers, which can enable distributed computing, such as cloud computing. The network 2030, in some cases with the aid of the computer system 2001, can implement a peer-to-peer network, which may enable devices coupled to the computer system 2001 to behave as a client or a server.

The CPU 2005 can execute a sequence of machine-readable instructions, which can be embodied in a program or software. The instructions may be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and writeback.

The CPU 2005 can be part of a circuit, such as an integrated circuit. One or more other components of the system 2001 can be included in the circuit. In some cases, the circuit is an application specific integrated circuit (ASIC).

The storage unit 2015 can store files, such as drivers, libraries and saved programs. The storage unit 2015 can store user data, e.g., user preferences and user programs. The computer system 2001 in some cases can include one or more additional data storage units that are located external to the computer system 2001 (e.g., on a remote server that is in communication with the computer system 2001 through an intranet or the Internet).

The computer system 2001 can communicate with one or more remote computer systems through the network 2030. For instance, the computer system 2001 can communicate with a remote computer system of a user (e.g., a doctor, a surgeon, a healthcare provider, a medical staff member, an operator of a surgical robot, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2001 via the network 2030.

Methods as described herein can be implemented by way of machine (e.g., computer processor) executable code stored on an electronic storage location of the computer system 2001, such as, for example, on the memory 2010 or electronic storage unit 2015. The machine executable or machine readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2001 can include or be in communication with an electronic display 2035 that comprises a user interface (UI) 2040 for providing, for example, a portal for a surgical operator to visualize one or more RGB images, infrared images, flow maps, and/or medical image overlays. In some cases, the one or more images, flow maps, and/or image overlays may comprise information (e.g., a thread tension value and/or a needle driver pressure value) pertaining to an operation of one or more medical tools. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2005. The algorithm may be configured to define a function space based at least in part on a first function corresponding to at least one laser speckle signal. In some cases, the algorithm may be further configured to compute one or more measurements for the function space. The one or more measurements may be defined in part based on a second function corresponding to a reference signal. In some cases, the algorithm may be further configured to generate an output signal in part based on the one or more measurements for the function space. The output signal may be used to aid a surgical procedure on or near the tissue region of the subject.

Laser Speckle Contrast Imaging

In another aspect, the present disclosure provides systems and methods for Laser Speckle Contrast Imaging (LSCI). LSCI is a non-scanning wide field-of-view optical technique utilized in a wide range of applications such as for imaging blood flow. When laser light illuminates a diffuse surface, the high coherence of the light produces a random granular effect known as speckle. Speckle patterns are generated on a target due to light interference which is spatially blurred due to the movement of scattering particles. Image frames containing the speckle patterns can be analyzed to compute dynamic and structural quantities of the target. However, conventional laser speckle contrast analysis (LASCA) methods can be computationally intensive, and/or require a large memory space for storing image frames.

The present disclosure provides systems and methods for LSCI with improved performance in computational speed and memory consumption. In some embodiments, the LSCI systems and methods disclosed herein can be used to generate an image depicting fluid (e.g., blood) flow of biological tissues in vivo with high spatial and temporal resolution. In particular, the systems and methods disclosed herein can provide a dynamic real-time method of processing speckle image frames. The method can employ algorithms for computing the statistics of the speckle image with reduced computation overhead and/or reduced memory consumption. The algorithms can be applied to raw speckle images to convert them to laser speckle contrast images in real-time without requiring memory space for storing intermediary/intermediate image frames.

In an aspect, a method is provided for improving laser speckle contrast imaging. The method comprises: irradiating laser light to a target region as a speckle pattern; capturing a series of speckle image frames each comprising speckle signals obtained from the scattered light of the target region illuminated by the laser light; and generating one or more laser speckle contrast maps by applying an infinite impulse algorithm to the series of speckle image frames.

In some embodiments, the series of speckle image frames are captured by a light signal detection unit. In some embodiments, the light signal detection unit comprises a CCD camera or CMOS camera. In some embodiments, applying the infinite impulse algorithm comprises computing a local speckle contrast value for each pixel by integrating the speckle signals in temporal, spatial domain or spatial-temporal domain using an infinite impulse integration. In some cases, the local speckle contrast value for a given pixel is calculated based on statistics values estimated by recursively summing the speckle signals in the preceding speckle image frames.

In some embodiments, the infinite impulse algorithm is selected from a group consisting of spatial infinite impulse algorithm, temporal infinite impulse algorithm and spatial-temporal infinite impulse algorithm. In some embodiments, the infinite impulse algorithm comprises a configurable parameter. In some cases, the method further comprises dynamically adjusting the configurable parameter based on a property of the target region. In some instances, the property of the target region comprises mobility of particles in the target region or the target region includes a tissue structure and the property comprises a type of the tissue.

In some cases, the local speckle contrast value is computed without division operation in some cases, integrating the speckle signals in the spatial domain comprises computing a recursive sum of speckle signals over neighboring pixels within a speckle image frame. In some instances, the neighboring pixels are within a 3×3 kernel. In some cases, computing a recursive sum of speckle signals over neighboring pixels comprises using an accumulator.

In another aspect, a system for laser speckle contrast imaging (LSCI) is provided. The system comprises: a light source configured to irradiate light to a target region; a light signal detection unit configured to capture a series of speckle image frames each comprising speckle signals obtained from the scattered light of the target region illuminated by the laser light; and one or more processors configured to generate one or more laser speckle contrast maps by applying an infinite impulse algorithm to the series of speckle image frames.

In some embodiments, the light signal detection unit comprises a CCD camera or CMOS camera. In some embodiments, applying the infinite impulse algorithm comprises computing a local speckle contrast value for each pixel by integrating the speckle signals in temporal, spatial domain or spatial-temporal domain using an infinite impulse integration. In some cases, the local speckle contrast value for a given pixel is calculated based on statistics values estimated by recursively summing the speckle signals in the preceding speckle image frames.

In some embodiments, the infinite impulse algorithm is selected from a group consisting of spatial infinite impulse algorithm, temporal infinite impulse algorithm and spatial-temporal infinite impulse algorithm. In some embodiments, the infinite impulse algorithm comprises a configurable parameter.

As described herein, the present disclosure provides systems and methods for Laser Speckle Contrast Imaging (LSCI). In particular, the provided systems and methods may be capable of producing laser speckle contrast images with improved speed and less computational overhead thereby enabling real-time imaging of fluid flow, motion of scattering particles or velocity of one or more underlying objects. Systems and methods of the present disclosure can be applied to a variety of areas such as retinal imaging, imaging of skin perfusion, imaging of neurophysiology and various non-clinical fields.

Laser Speckle Contrast Imaging (LSCI) is an optical technique useful for the characterization of scattering particle dynamics with high spatial and temporal resolution. In some embodiments, LSCI can be used to generate an image depicting blood flow of biological tissues in vivo with high spatial and temporal resolution. There exist conventional methods and algorithms for processing raw speckle images to convert them to laser speckle contrast images. However, such conventional methods can be computationally intensive and may not be suitable for real-time imaging.

In some embodiments, fluid flow or velocity of objects being imaged can be obtained by processing speckle pattern of the target site. The speckle pattern can arise from the random interference of coherent light (e.g., laser). When collecting laser speckle contrast images, coherent light is used to illuminate a target site/region (e.g., sample, tissue, organ in human body, etc.) and a photodetector is then used to receive light that has scattered from varying positions within the target site/region. The light may have traveled a distribution of distances, resulting in constructive and destructive interference that varies with the arrangement of the scattering particles with respect to the photodetector. When this scattered light is imaged onto a camera, it produces a randomly varying intensity pattern known as speckle. If scattering particles are moving, this will cause fluctuations in the interference, which will appear as intensity variations at the photodetector. The temporal and spatial statistics of this speckle pattern provide information about the motion of the underlying object being imaged.

Conventional laser speckle contrast analysis (LASCA) methods can be computationally expansive, and/or require a large memory space for storing image frames. Fluid velocity can be computed by speckle contrast value which is (directly or indirectly) proportional to the velocity of the target or underlying object being imaged. The speckle contrast can be conventionally computed as the ratio of the standard deviation to the mean of the intensities over a pixel window. The pixel window can be spatial window (e.g., a square region of pixels from a single image), temporal window (the same pixel over multiple frames in time), or a combination of the both, spatiotemporal (e.g., a square region of pixels over multiple frames. For instance, there are two conventional laser speckle contrast analysis (LASCA) methods used to compute the spatially localized speckle contrast, being the spatial LASCA and temporal LASCA. The spatial LASCA method involves obtaining a contrast map which is coarsed in respect to original one by the size of the neighborhood area used for local averaging (e.g., 5×5 pixels in size). The speckle contrast value is quantified by the usual parameter of the ratio of the standard deviation to the mean of the intensities for each pixel in the local neighborhood. The temporal LASCA method utilizes the temporal sequence of pixels taken from the location of a sequence of image frames. The speckle contrast value is computed as the standard deviation of time-integrated intensity divided by the mean time-integrated intensity over a temporal pixel window. However, these conventional LASCA methods can be computationally expansive, and/or require large memory space for storing the intermediate frames.

Figure 9:
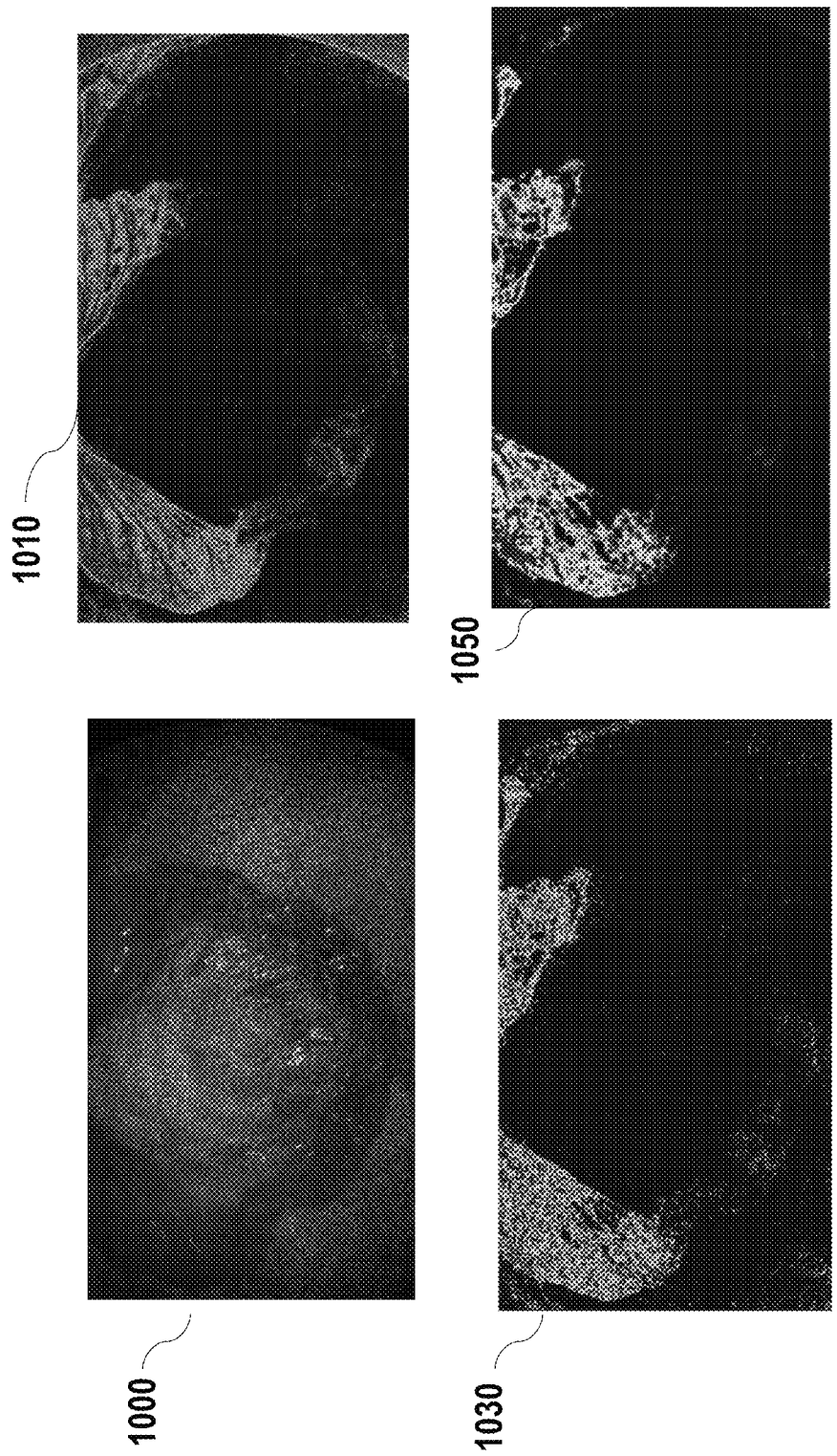
FIG. 9 shows an example of a raw speckle image, and laser speckle contrast images produced using conventional algorithms.

FIG. 9 shows an example of a raw speckle image 1000, and laser speckle contrast images 1010, 1030, 1050 produced using conventional algorithms. The raw speckle image 1000 shown in FIG. 9 illustrates the grainy appearance of the speckle pattern. In the raw speckle image 1000, more pronounced speckle may indicate lower velocity (e.g., less blood flow).

The laser speckle contrast image 1010, 1030, 1050 are computed directly from a sequence of raw speckle images or image stream using conventional LSCI and LASCA algorithms with different pixel window size, representing a 2-D map of blood flow. For instance, areas of higher baseline flow, such as large vessels, have lower speckle contrast values and appear darker in the speckle contrast images.

The raw speckle image 1000 or raw speckle image stream can be captured by an imaging device such as a camera. The imaging device may be a digital camera, a video camera, charge coupled device (CCD) image sensor, or a complementary metal oxide semiconductor (CMOS) image sensor.

The speckle as illustrated in FIG. 9 arises from the random interference of coherent light such as laser. The raw speckle image data generated by an imaging device can include one or more images, which may be dynamic images (e.g., video). The image data can be polychromatic (e.g., RGB, CMYK, HSV) or monochromatic (e.g., grayscale, black-and-white, sepia). The image data may have various sizes dependent on the image frame resolution. The image frame resolution may be defined by the number of pixels in a frame. In some examples, the image resolution may be greater than or equal to about 128×128 pixels, 32×32 pixels, 64×64 pixels, 88×72 pixels, 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, or 15360×8640 pixels. The raw speckle image data can be captured at a frame rate. In the illustrated example, the raw speckle image 100 is an image frame captured at a frame rate of 120 frames per second.

Speckle contrast is a measure of the local spatial contrast in the speckle pattern. Typically, a higher contrast value indicates higher flow or motion, and a lower value indicates less flow or motion. The speckle contrast may be a function of the exposure time of the camera.

A spatially resolved map of local speckle contrast such as speckle contrast images 1030, 1050 can be calculated from one raw speckle image or a sequence of raw speckle images by computing this ratio at each point in the image from the pixels over a local neighborhood of the pixel within an image, which is referred to as a window or spatial neighborhood area.

The speckle contrast images 1030, 1050 are produced by processing the raw speckle image 1000 using a conventional spatial LASCA algorithm. The length of the window in pixels is represented by M (assuming the window is square). M is a natural number such as between 5 and 20. The speckle contrast image 1030 is produced with M equal to 5 and speckle contrast image 1050 is produced with M equal to 10. The width and height of a raw speckle image in pixels is represented by W (columns) and H (rows) and, respectively. The spatial contrast images 1030, 1050 can be generated using the below equation:

$$\mu_i^{LASCA}(x, y) = \frac{1}{(1+2M)^2} \sum_{x-M \le i \le x+M, y-M \le k \le y+M} I_i(j, k)$$

$$\xi_i^{LASCA}(x, y) = \frac{1}{(1+2M)^2} \sum_{x-M \le j \le x+M, y-M \le k \le y+M} (I_i(j, k))^2$$

$$\sigma_i^{LASCA}(x, y) = \xi_i^{LASCA}(x, y) - (\mu_i^{LASCA}(x, y))^2$$

$$C_i^{LASCA}(x, y) = \frac{(\mu_i^{LASCA}(x, y))^2}{(\sigma_i^{LASCA}(x, y))^2}$$

where I (x, y) represents the intensity for the pixel (x, y) and $C_i^{LASCA}$(x, y) represents the spatial contrast value for pixel (x, y) in the spatial contrast images 1030, 1050. The statistics mean value $\mu_i^{LASCA}$ and variance $\xi_i^{LASCA}$ are computed for the local neighborhood area (M×M) and the spatial contrast value is computed by dividing mean value by the standard deviation.

The speckle contrast image 1010 is produced by processing the raw speckle image 1000 using a conventional temporal LSCI algorithm. In the example, the length of the window in temporal domain will be represented by M (M number of frames). M represents the number of frames over which the statistics of local contrast is computed (e.g., a number between 10 and 20). The illustrated speckle contrast image 1010 is produced with M equal to 15. The width and height of a raw speckle image(s) in pixels is represented by W (columns) and H (rows) and, respectively. The temporal contrast image 1010 can be generated using the below equation:

$$\mu_i^{LSCI}(x,y) = \frac{1}{M} \sum_{i-M<j\leq i} I_j(x,y)$$

$$\xi_i^{LSCI}(x,y) = \frac{1}{M} \sum_{i-M<j\leq i} (I_j(x,y))^2$$

$$\sigma_i^{LSCI}(x,y) = \xi_i^{LSCI}(x,y) - (\mu_i^{LSCI}(x,y))^2$$

$$C_i^{LSCI}(x,y) = \frac{(\mu_i^{LSCI}(x,y))^2}{(\sigma_i^{LSCI}(x,y))^2}$$

where I (x, y) represents the intensity for the pixel (x, y) and $C_i^{LSCI}$(x, y) represents the temporal contrast value for pixel (x, y) in the temporal contrast image 1010. The statistics mean value $\mu_i^{LSCI}$ and variances $\xi_i^{LSCI}$ are computed for the temporal window (e.g., M frames centered at frame i) and the temporal contrast value is computed by dividing the mean value by the standard deviation.

As mentioned above, the present disclosure provides laser speckle contrast algorithms for the computation of a laser speckle contrast image from a raw speckle image. In particular, the laser speckle contrast algorithms disclosed herein utilize infinite impulse integration or exponential moving average (EMA) filter to process the raw speckle image. Unlike conventional methods where finite sums are computed for the contrast value, utilizing a recursive filter (e.g., EMA) as disclosed herein may beneficially reduce the computational overhead and achieve/enable real-time imaging. The exponential moving average filter described herein is a weighted combination of the previous estimate (output) with the newest input data, with the sum of the weights equal to 1 so that the output matches the input at steady state. The infinite impulse integration method may beneficially allow the statistics computed using a recursive implementation such that the computationally-intensive division operator can be avoided. Furthermore, the EMA filter described herein can be dynamically adjusted to adapt to different scenarios or real-time conditions.

The present disclosure provides several laser speckle contrast algorithms that perform the infinite impulse integration in the spatial domain, temporal domain and a spatial-temporal domain. The laser speckle contrast algorithms disclosed herein can require less computational resources, and/or require less memory space for storing image frames compared to the conventional algorithms described earlier with reference to FIG. 9. A description of each algorithm in accordance with embodiments of the present disclosure is described below.

The temporal infinite impulse integration (III) algorithm may be capable of estimating the statistics μ and σ in real-time without requiring significant computational overhead (e.g., CPU cache) for storing intermediate raw speckle images, when compared to the conventional temporal LSCI algorithm. The statistics μ and σ can be computed for each new speckle image streaming in with reduced latency. The EMA filter in the temporal domain also imposes a low-pass filter on the raw speckle image stream which has improved accuracy in the result compared to the conventional (e.g., finite integration) LSCI algorithm which has "ringing" temporal artifacts across frames due to the box window filter imposed by uniformly weighting all frames.

The temporal infinite impulse integration algorithm may apply an exponential moving average (EMA) filter to the raw speckle image.

The EMA filter includes a time constant α (a.k.a, decay rate) which is a value between 0 and 1. The value of the time constant α may correspond to the smoothing effect. A smaller value (e.g., α=0.65) may indicate more weight is assigned to recent past image frames whereas a greater value (e.g., α=0.8) represents the effective time over which the average is estimated increases. The value of the time constant α can be predetermined based on empirical data or set by a user. Alternatively or in addition, the value of the time constant α may be tuned based on the object being imaged or property of the target region being imaged (e.g., mobility or velocity of the particles in the target region, a tissue structure, a type of the tissue) or a desired video/image quality (e.g., mitigating artifacts such as noise, blur, etc.).

The contrast value can be computed using the below equation:

$$\mu_0^{TIII}(x,y) = I_0(x,y)$$

$$\mu_i^{TIII}(x,y) = (1-\alpha)*I_i(x,y) + (\alpha)*\mu_{i-1}^{TIII}(x,y)$$

$$\xi_0^{TIII}(x,y) = (I_0(x,y))^2$$

$$\xi_i^{TIII}(x,y) = (1-\alpha)*(I_i(x,y))^2 + (\alpha)*\xi_{i-1}^{TIII}(x,y)$$

where the mean value $\mu_i^{TIII}$ and variance $\xi_i^{TIII}$ is estimated using the recursive equation, respectively. The contrast value is then computed as the ratio of the mean to the standard deviation. Using the above recursive equation may beneficially avoid the use of computationally-intensive division operators. For example, as the number of samples increases, the contrast value $$C = \frac{\mu^2}{\sigma^2}$$

approaches $$C = \frac{\mu_i^2}{\xi_i^2 - \mu_i^2}$$

which simplifies the computational complexity compared to conventional methods.

The spatial infinite impulse integration (III) algorithm is applied to a single raw speckle image frame iteratively to generate a contrast image, similar to a heat diffusion process. The heat diffusion-like process is iteratively applied to the entire raw speckle image frame such that information/influence of each pixel spreads from pixel to pixel until it has diffused over the entire contrast image, and pixels close to a given pixel are weighted more in the estimation of the statistics (e.g., mean value μ and variance ξ).

The spatial III algorithm may include a space constant β that controls the rate of the diffusion. A greater value of the space constant β may indicate more influence of the preceding pixels being taken into account and thus a greater diffusion rate. The value of the space constant β can be predetermined based on empirical data or by a user. Alternatively or in addition to, value of the space constant β may be tuned based on the property of the object or target region being imaged (e.g., type of tissue), desired image processing performance (e.g., computation speed, etc.) or a desired video/image quality (e.g., mitigating artifacts such as noise, blur, etc.).

The spatial infinite impulse integration algorithm may be more computationally efficient than the conventional spatial LASCA method. The spatial infinite impulse integration algorithm may utilize an accumulator A or virtual frame buffer to accumulate counts over time. For example, an accumulator $A^\mu$ and an accumulator $A^\xi$ may be used to hold the counts for the mean value $\mu$ and variance $\xi$ respectively. Set $\mu^{SIII}=A_M^\mu$, and $\xi^{SIII}=A_M^\xi$. M is a natural number that controls the number of iterations allowing the diffusion to occur over and a space constant $\beta$ controls the rate of the diffusion. As an example, M may be in the range of 10-20. As the number of iterations M increases, the impulse response may approach a Gaussian profile and each pixel is influenced by more neighboring pixels. A small number of iterations M tend to result in more artifacts. The statistics of the speckle image can be computed using the below equations:

$$A_0^\mu(x,y)=I_0(x,y)$$

$$A_i^\mu(x,y)=1/9($$

$$(1-\beta^*($$

$$A_{i-1}^\mu(x-1,y-1)+A_{i-1}^\mu(x,y-1)+A_{i-1}^\mu(x+1,y-1)+$$

$$A_{i-1}^\mu(x-1,y)+A_{i-1}^\mu(x+1,y)+$$

$$A_{i-1}^\mu(x-1,y+1)+A_{i-1}^\mu(x,y+1)+A_{i-1}^\mu(x+1,y+1)$$

$$)+$$

$$(\beta)^*(A_{i-1}^\mu(x,y))$$

$$)$$

$$A_0^\xi(x,y)=(I_0(x,y))^2$$

$$A_i^\xi(x,y)=1/9($$

$$(1-\beta^*($$

$$A_{i-1}^\xi(x-1,y-1)+A_{i-1}^\xi(x,y-1)+A_{i-1}^\xi(x+1,y-1)+$$

$$A_{i-1}^\xi(x-1,y)+A_{i-1}^\xi(x+1,y)+$$

$$A_{i-1}^\xi(x-1,y+1)+A_{i-1}^\xi(x,y+1)+A_{i-1}^\xi(x+1,y+1)$$

$$)+$$

$$(\beta)^*(A_{i-1}^\xi(x,y))$$

$$)$$

$$\mu^{SIII}=A_M^\mu \text{ and } \xi^{SIII}=A_M^\xi$$

The spatial infinite impulse integration algorithm may be capable of generating a single contrast image from a single raw speckle image by allowing the statistics of the single raw speckle image to spread out via the aforementioned heat diffusion-like process. This beneficially replaces the division operation required for the conventional method, which simplifies the computational complexity.

The spatial-temporal infinite impulse integration (III) algorithm is a combination of the temporal III and spatial III algorithm. The process may apply the spatial-temporal infinite impulse integration algorithm to a series of speckle images $I_i$ and generate a sequence of contrast images $C_i$. Each contrast image $C_i$ may be generated using the preceding speckle images $I_j$, $j \le i$. The spatial-temporal infinite impulse integration algorithm may also use an accumulator $A^\mu$ and an accumulator $A^\xi$ to hold the counts for the mean value $\mu$ and variance $\xi$, respectively. In an exemplary process, the method may begin with computing $\mu^{TIII}$ using the temporal III algorithm with the time constant $\alpha$ specified. Next, the mean value $\mu^{S-TIII}$ is computed as a recursive sum in both the spatial and temporal domain. For example, accumulator $A_i^\mu$ is computed by folding $\mu_i^{TIII}$ and $A_{i-1}^\mu$ into $A_i^\mu$ with a space constant $\beta$ specified. The mean value $\mu^{\mu S-TIII}$ can be computed according to the below equations:

$$A_0^\mu(x,y)=\mu_0^{TIII}(x,y)$$

$$A_i^\mu(x,y)=1/9($$

$$(1-\beta^*($$

$$A_{i-1}^\mu(x-1,y-1)+A_{i-1}^\mu(x,y-1)+A_{i-1}^\mu(x+1,y-1)+$$

$$A_{i-1}^\mu(x-1,y)+A_{i-1}^\mu(x+1,y)+$$

$$A_{i-1}^\mu(x-1,y+1)+A_{i-1}^\mu(x,y+1)+A_{i-1}^\mu(x+1,y+1)$$

$$)+$$

$$(\beta)^*(\mu_{i-1}^{TIII}(x,y))$$

$$)$$

The statistic value $\xi^{S-TIII}$ can be calculated in a similar process to the above. The above method beneficially replaces the division operation required for the conventional method, which simplifies the computational complexity.

The spatial III algorithm, temporal III algorithm and spatial-temporal III algorithm disclosed herein can enable improved performance (e.g. in memory consumption) as these algorithms need not require large memory space to store the intermediary image frames. Using the above algorithms disclosed herein, data can flow efficiently among the processor's registers, arithmetic logic units, floating point units, and other digital circuits with considerably less use of the cache and significantly less likelihood of needing to access main memory (it is noted that heavy reliance and use of the cache and main memory can substantially increase burden on computation time). Although implementing the Spatial III algorithm or the spatial-temporal III algorithm requires an accumulator, the memory consumption is still much lower compared to conventional methods. For instance, the size of the accumulator is the size of a single image whereas the memory consumption for the conventional method is on the order of tens to hundreds of images without the accumulator, with additional required processing time proportional to the space requirements. The memory unit can be any suitable RAM including static random-access memory (SRAM), dynamic random-access memory (DRAM), synchronous dynamic random-access memory (SDRAM), double data rate (DDR), double data rate synchronous dynamic random-access memory (DDR SDRAM), DDR, DDR2, DDR3, T-RAM, Z-RAM, and so forth.

The infinite impulse integration algorithms disclose herein can be utilized in a wide range of applications. In some cases, the temporal III algorithm may be used in combination with a reference signal to measure correlation with a known target (e.g., the pulse of a human to detect motion due to a heartbeat or a synthesized heterodyne vibration). This can be advantageous for distinguishing motion in the imaged scene caused by the underneath fluid flow or a motion of the tissue (e.g., respiration and heart beating). For example, a reference measurement P of the contrast value C against a reference signal R can be calculated using the below equation:

$$P_0(x,y)=C_0(x,y)^*R_0(x,y)$$

$$P_i(x,y)=(1-\alpha)^*C_i(x,y)^*R_i(x,y)+(\alpha)^*P_{i-1}(x,y)$$

In some embodiments, the present disclosure provides methods for generating the speckle contrast image by implementing the temporal III algorithm, Spatial III algorithm or the spatial-temporal III algorithm. The methods disclosed herein may beneficially improve speckle contrast image quality, mitigate artifacts (e.g., noise, blur) and/or improve the temporal/spatial resolution. For example, a method of processing the raw speckle image using the temporal III algorithm may advantageously generate contrast images at a rate that is the same as (or similar to) the frame rate for acquiring the raw speckle images, while reducing the artifacts caused by spatial noise or motion blur. The produced contrast image may have reduced spatial noise and/or reduced motion blur compared to the contrast image generated using conventional methods because more image frames are used for estimating the statistics and the influence of the image frames is optimized by applying more weight to the closer image frames (e.g., image frames closely preceding a given frame). In another example, a method of processing the raw speckle image using the spatial III algorithm may advantageously generate contrast images with improved temporal resolution and/or reduced spatial noise, given that a contrast image can be generated using a single raw speckle image and the spatial noise may not be carried over from frame to frame. In a further example, a method of processing the raw speckle image using the spatial-temporal III algorithm may advantageously generate contrast images with improved temporal resolution, spatial resolution as well as reduced temporal noise and spatial noise. In some situations, the method of utilizing the spatial-temporal III algorithm may have an improved contrast image quality over the method of using either the spatial III algorithm or the temporal III algorithm alone.

Figure 10:
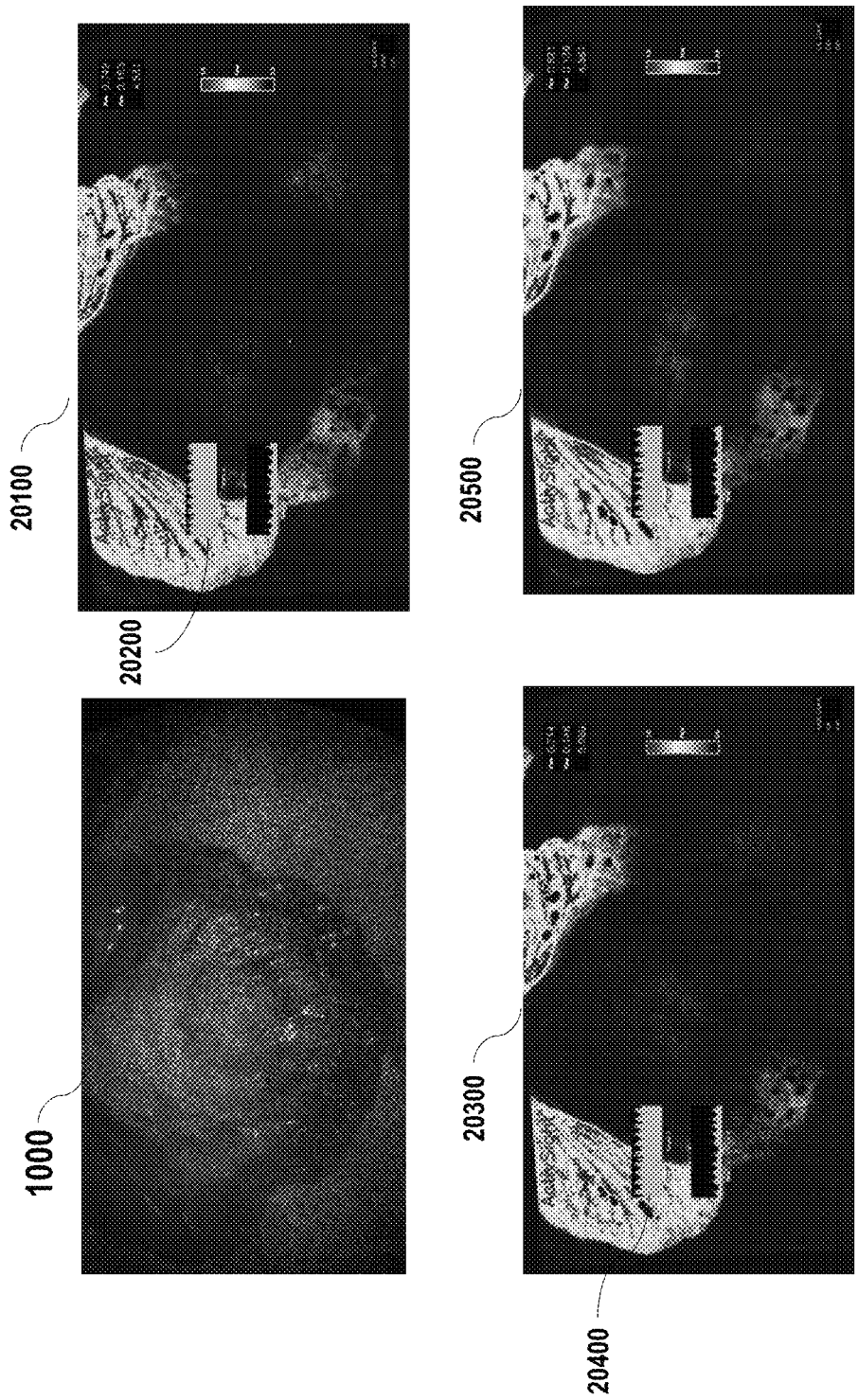
FIG. 10 shows an example of a raw speckle image, and laser speckle contrast images produced using a temporal infinite impulse integration (III) algorithm, spatial III algorithm and spatial-temporal III algorithm, respectively, in accordance with some embodiments of the disclosure.

FIG. 10 shows an example of a raw speckle image 1000, and laser speckle contrast images 20100, 20300, 20500 produced using the temporal III algorithm, spatial III algorithm and spatial-temporal III algorithm, respectively. The raw speckle image 1000 is the same as the speckle image as shown in FIG. 9. The laser speckle contrast image 20100, 20300, 20500 are computed directly from a raw speckle image, and a sequence of raw speckle images using the temporal III algorithm, spatial III algorithm, and spatial-temporal III algorithm as described above.

The speckle contrast image 20100 may be generated by applying the temporal III algorithm to a sequence of raw speckle images preceding a given raw speckle image (e.g., raw speckle image 1000). Unlike the conventional method where a speckle contrast image is generated using a sequence of image frames in a temporal window centered at a given raw speckle image (e.g., requiring both the preceding image frame and subsequent image frames), the speckle contrast image 20100 can be generated upon the raw speckle image 1000 being captured thereby eliminating the imaging latency. This may beneficially allow a speckle contrast image 20100 to be produced at a rate that is the same as (or similar to) the rate as the raw speckle image is being captured. Moreover, as shown in the example, the speckle contrast image 20100 may exhibit higher image quality such as less spatial noise and/or motion blur compared to the speckle contrast image (e.g., contrast image 1010 with M=15) generated using the conventional temporal LSCI algorithm. This is because more image frames (all the preceding image frames) are used in the temporal III algorithm for estimating the statistics and the influence of the image frames is optimized by applying more weight to the closer image frames (e.g., image frames closely preceding a given frame).

The speckle contrast image 20300 may be generated by applying the spatial III algorithm to a given raw speckle image (e.g., raw speckle image 1000). As shown in the example, the speckle contrast image 20300 may exhibit higher image quality compared to the speckle contrast image (e.g., contrast image 1030 with M=5, contrast image 1050 with M=10) generated using the conventional spatial LASCA algorithm. Compared to the temporal contrast image 20100 produced by the temporal III algorithm, the speckle contrast image 20300 demonstrates less spatial noise as well as less spatial details (e.g., vessels can be hard to perceive). The temporal resolution may be improved (quantified by the contrast 20200, 20400 of signals over time) over the temporal III algorithm; however the variation of noise may also be greater i.e., greater temporal noise.

The speckle contrast image 20500 may be generated by applying the spatial-temporal III algorithm to a sequence of raw speckle images preceding a given raw speckle image (e.g., raw speckle image 1000). As shown in the example, the speckle contrast image 20500 may exhibit improved image quality over the contrast image generated using either the temporal III algorithm or spatial III algorithm. As shown in the example, the temporal resolution is as high as using the spatial III algorithm while the temporal noise is lower than the spatial III algorithm. Additionally, the spatial resolution is maintained as more spatial details are visible while the spatial noise is reduced due to the smoothness introduced by the temporal integration.

In some embodiments, the methods disclosed herein may be adaptive to real-time conditions. For example, one or more parameters of the algorithms disclosed herein can be dynamically adjusted. For example, the time constant and/or space constant may be determined dynamically based on a desired video/image quality (e.g., smoothing requirement), property of the target region or object being imaged (e.g., mobility of the particle, velocity of the object, type of tissue, tissue structures, etc.), imaging parameters (e.g., frame rate) or various other conditions (e.g., computational power consumption, hardware requirement, etc.). In some cases, an initial value of the time constant $\alpha$ may be determined based on empirical data or predetermined by a user, and tuned based on the property of the target region or object being imaged (e.g., mobility or velocity of the object being imaged) or a desired video/image quality (e.g., mitigating artifacts such as noise, blur, etc.) in real-time.

Figure 11:
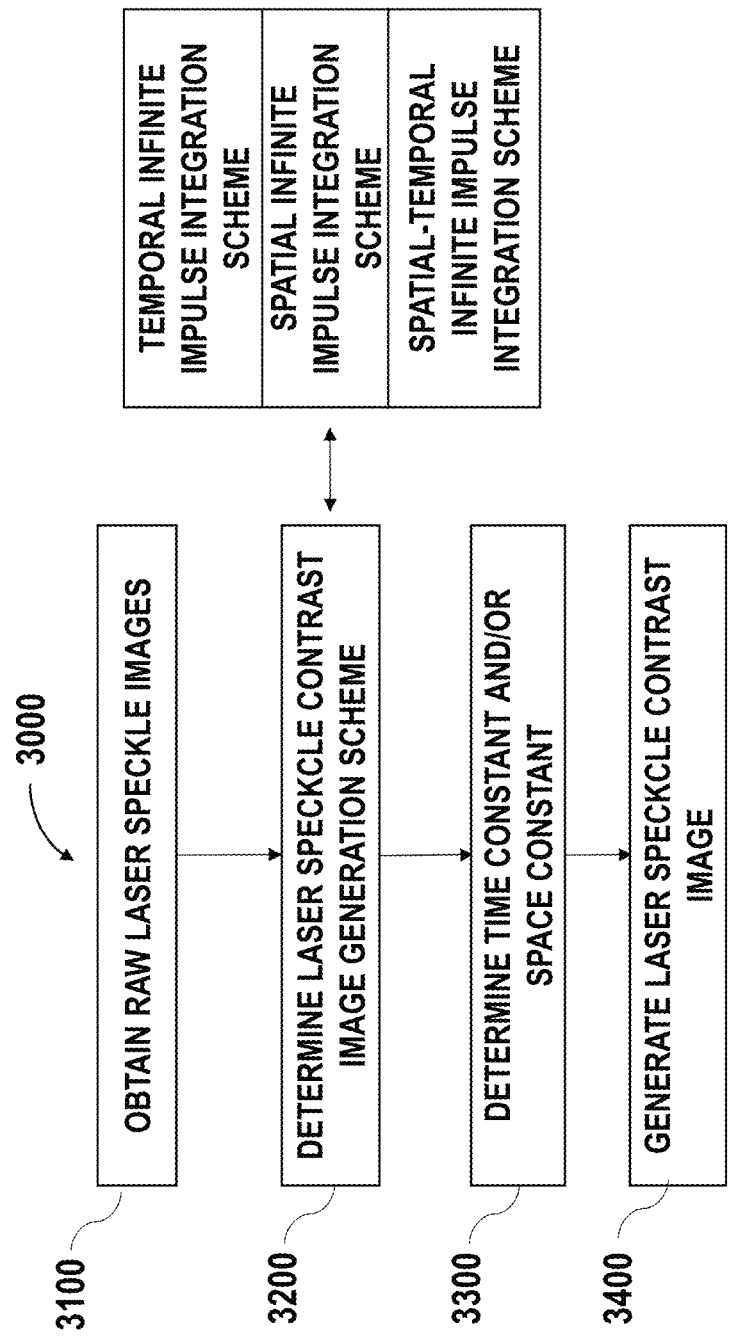
FIG. 11 shows an example of method for producing a laser speckle contrast image or flow map, in accordance with some embodiments of the disclosure.

FIG. 11 shows an example of a process for producing a laser speckle contrast image or flow map 3000, in accordance with some embodiments. The process may begin with obtaining raw laser speckle image (step 3100). Next, a laser speckle contrast image generation scheme may be determined (step 3200) for generating a laser contrast image. For example, a laser speckle contrast image generation scheme may be selected from the temporal infinite impulse integration (e.g., temporal III) scheme, spatial infinite impulse integration (e.g., spatial III) scheme and a spatial-temporal infinite impulse integration (e.g., spatial-temporal III) scheme. A laser speckle contrast image generation scheme may specify the algorithm for processing the raw speckle image (e.g., temporal III algorithm, spatial III algorithm, spatial-temporal III algorithm) and an initial/default value of one or more parameters (e.g., time constant, space constant, etc.).

In some cases, a value of the one or more parameters may be determined (step 3300) for the laser speckle contrast image generation scheme. For example, the value of the time constant or space constant may be specified by a user for a desired smoothing effect or image processing speed, and/or dynamically adjusted based on a property of the captured raw speckle images without user intervention. Upon determining the time constant and/or space constant associated with the selected laser speckle contrast image generation scheme, a laser speckle contrast image may be generated (step 3400) and output to a display device.

For instance, mobility of an object present in the raw speckle image may be determined (e.g., detected in real-time, estimated based on tissue type, etc.), and based on the mobility state (e.g., velocity, stationary and the like), a time constant value may be determined. For instance, if the object being imaged tends to be still, a greater value may be set for the time constant to achieve a better smoothing result (e.g., less spatial noise) whereas if the object is in motion or capable of being in motion, a smaller value may be set for the time constant to reduce motion blur. The value of the space constant may also be adjusted based on a noise distribution property of the captured raw image data and/or desired processing speed. Such adjustment or attenuation may be performed automatically without user intervention. For example, a relationship between the time/space constant and the raw speckle image properties or the target region property may be pre-determined (e.g., using empirical data) such that the time/space constant can be adjusted automatically.

In some case, a user may be allowed to define a laser speckle contrast image generation scheme in a semi-autonomous fashion. A user may specify one or more parameters of a selected laser speckle contrast image generation scheme. In some cases, in response to receiving the laser speckle contrast image generation scheme, contrast images may be generated and output to a display for the user to visualize. A user may or may not further adjust the laser speckle contrast image generation scheme so as to change the quality or other characteristics of the output images. In some instances, a user may be provided with a system-recommended adjustment. In some instances, a user may manually adjust one or more parameters upon viewing the output images on a display. For example, a user may be presented a real-time output contrast image and a recommended (e.g., simulated) higher quality image that can be achieved under the system-recommended parameters. In some cases, the real-time output contrast image or simulated images may be dynamically updated while the user is adjusting one or more parameters of the laser speckle contrast image generation scheme.

Although FIG. 11 shows a method in accordance with some embodiments, a person of ordinary skill in the art will recognize that there are many adaptations for various embodiments. For example, the operations can be performed in any order. Some of the operations may be precluded, some of the operations may be performed concurrently in one step, some of the operations repeated, and some of the operations may comprise sub-steps of other operations. For example, the operation of determining a laser speckle contrast image generation scheme 3200 can be performed prior to or concurrently with capturing raw laser speckles or repeated for a new image acquisition session. In another example, the operation of selecting time constant and/or space constant may be performed prior to capturing raw laser speckles or repeated for a new image acquisition session.

Figure 12:
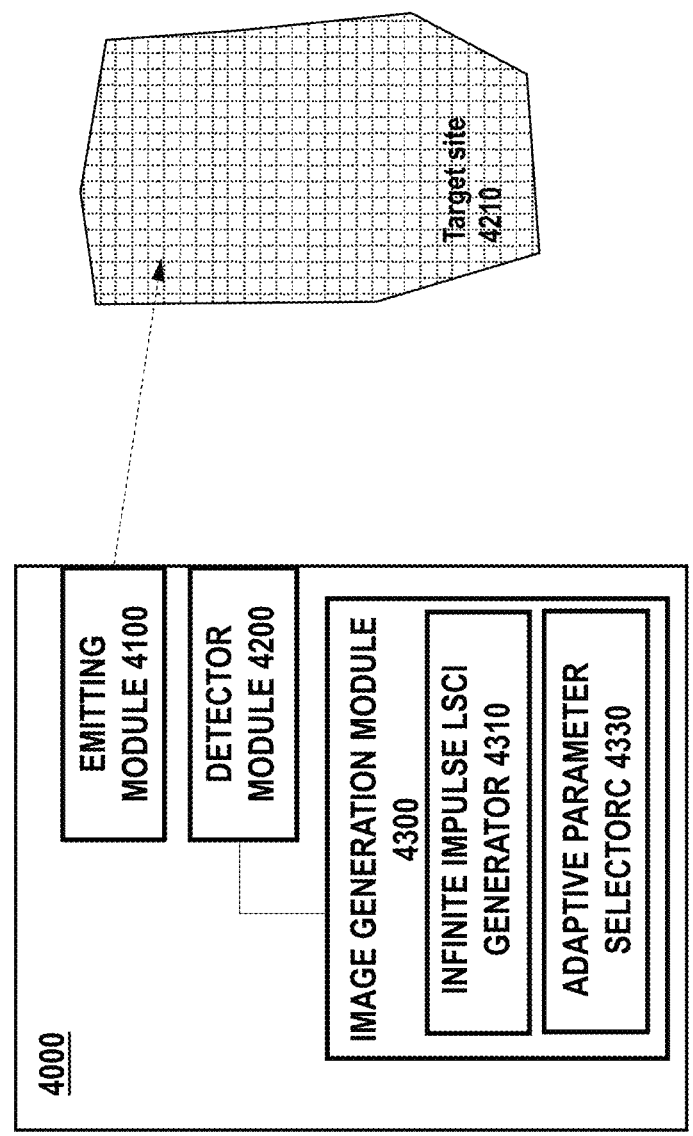
FIG. 12 schematically illustrates a system implementing the methods and algorithms described herein, in accordance with some embodiments of the disclosure.

FIG. 12 schematically illustrates a system 4000 implementing the methods and algorithms described herein, in accordance with some embodiments of the disclosure. The system 4000 may comprise an emitting module 4100, a detector module 4200, and an image generation module 4300 that are operably coupled to each other for laser speckle contrast imaging. In some embodiments, the system 4000 may be capable of determining a fluid flow rate within a target site 4210.

The detector module 4200 may be configured to obtain one or more speckle images of a target site. The target site 4210 may comprise a portion of an organ of a patient or an anatomical feature or structure within a patient's body. The target site 4210 may comprise a surface of a tissue of the patient's body. The surface of the tissue may comprise epithelial tissue, connective tissue, muscle tissue (e.g., skeletal muscle tissue, smooth muscle tissue, and/or cardiac muscle tissue), retina, the cerebral cortices and/or nerve tissue. The captured images may be processed to obtain fluid flow information of the target site 4210. In some embodiments, the fluid is blood, sweat, semen, saliva, pus, urine, air, mucus, milk, bile, a hormone, or any combination thereof. In some embodiments, the fluid flow rate within the target tissue is determined by a contrast map or contrast image generated using the methods described above.

The emitting module 4100 may comprise a coherent light source, such as a laser diode, whose beam is expanded and adjusted to illuminate the target site 4210, which can vary from a few millimeters to several centimeters. The angle of the incident light may range from near normal incidence to as much as 45°. The light source may be configured to operate in a continuous mode or a pulse mode. In some cases, the operation mode or wavelengths of the light may depend on a distance to the target site, object to be imaged and other properties of the target site. For example, the emitting module may be a device that generates light in a near-infrared spectrum range. When compared to a laser in a visible light range, the laser in the near-infrared range (around a wavelength of about 980 nm) is substantially scattered by red corpuscles and noise scattering from an outer layer occurs less. Thus, by using the light in the near-infrared spectrum range, the detector module 4200 may accurately receive information about a bloodstream in a blood vessel located deeper than skin or a capillary and may be less affected by the skin or the capillary.

The detector module 4200 may be configured to obtain one or more speckle images of a target site. The captured speckle images may be processed by the image generation module to generate contrast image or provide information about fluid flow within the target site with improved temporal and/or spatial resolution. The detector module 4200 may include an optical sensor. The optical sensor may be, but not limited to, e.g., a charge coupled device (CCD), a complementary metal-oxide semiconductor (CMOS), a linear image sensor, an array silicon-type image sensor, or an InAsGa sensor. The detector module 4200 may convert the intensity of the scattered light into a digital signal. The detector module may include an imaging device as described above. For example, the imaging device may comprise a camera, a video camera, a Red Green Blue Depth (RGB-D) camera, an infrared camera, a near infrared camera, a charge coupled device (CCD) image sensor, or a complementary metal oxide semiconductor (CMOS) image sensor.

The imaging sensor may be capable of capturing an image frame or a sequence of image frames at a specific image resolution. The image frame resolution may be defined by the number of pixels in a frame. The image resolution may be greater than or equal to about 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, 1536×1536, or 1536×8640 pixels. The imaging device may be, for example, a 4K camera or a camera with a higher resolution.

The imaging sensor may capture a sequence of raw speckle images at a specific capture rate. In some cases, the sequence of images may be captured at standard video frame rates. The provided system 4000 may achieve real-time laser speckle contrast imaging with minimal latency. For example, the raw image data may be processed and contrast map may be generated in real-time at a speed greater than or equal to 20, fps, 30 fps, 40 fps, 50 fps, 100 fps, 150 fps, 200 fps at resolution greater than or equal to about 352×420 pixels, 480×320 pixels, 720×480 pixels, 1280×720 pixels, 1440×1080 pixels, 1920×1080 pixels, 2008×1508 pixels 2048×1080 pixels, 3840×2160 pixels, 4096×2160 pixels, 7680×4320 pixels, or 15360×8640 pixels.

In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) that can be further processed by a camera circuit or processors of the camera. In some cases, the image sensor may comprise an array of optical sensors.

In some cases, the detector module 4200 may perform pre-processing of the captured raw speckle image data. In an embodiment, the pre-processing algorithm can include image processing algorithms, such as image smoothing, to mitigate the effect of sensor noise, or image histogram equalization to enhance the pixel intensity values.

The image generation module 4300 may execute one or more algorithms consistent with the methods disclosed herein to generate contrast images or flow maps. In some embodiments, the image generation module 4300 may comprise an infinite impulse LSCI generator 4310 implementing an infinite impulse integration algorithm (e.g., spatial III algorithm, temporal III algorithm, spatial-temporal III algorithm) described herein to generate laser speckle contrast images. One or more of the algorithms may be applied to the real-time speckle image data to produce the desired fluid flow information. The image generation module 4300 may also comprise an adaptive parameter selector 4330 for determining the one or more parameters associated with the infinite impulse integration algorithm.

For example, the adaptive parameter selector 4330 may be capable of determining a value for the time constant for the temporal III algorithm or spatial-temporal III algorithm, a value for the space constant for the spatial III algorithm or the spatial-temporal III algorithm as described above. The adaptive parameter selector 4330 may be configured to determine or adjust a value of the time constant or space constant automatically without user intervention as elsewhere herein. In some embodiments, the adaptive parameter selector 4330 may be operably coupled to a user interface allowing a user to determine a value of the one or more parameters.

The user interface may be configured to receive user input and display output information to a user. The user input may be related to controlling or setting up a laser speckle contrast image generation scheme or one or more parameters. For example, the user input may indicate a value of the time constant, space constant, selection of a laser speckle contrast image generation scheme and the like. In some cases, the user interface may also allow users to specify image acquisition parameters. For example, the user input may indicate frame rate, light source operation mode for each acquisition/run and the like.

In some cases, the user interface may allow users to adjust one or more parameters at any stage of the image acquisition. A user may set up the parameters prior to or during image acquisition. In some cases, in response to receiving the laser speckle contrast image generation scheme, the image generation module 4300 may produce contrast images and output the contrast images to the user interface for display. A user may or may not further adjust the laser speckle contrast image generation scheme so as to change the quality or other characteristics of the output images. In some instances, a user may be provided with system-recommended adjustment on the user interface. In some instances, a user may manually adjust one or more parameters upon visualizing the output images on a display. For example, a user may be presented a real-time contrast image and a recommended (simulated) higher quality image that can be achieved under the system-recommended parameters. In some cases, the real-time output contrast image or simulated images may be dynamically updated while the user is adjusting one or more parameters of the laser speckle contrast image generation scheme.

In some cases, the real-time contrast images may be rendered on a graphical user interface (GUI). The GUI may be provided on a display. The display may or may not be a touchscreen. The display may be a light-emitting diode (LED) screen, organic light-emitting diode (OLED) screen, liquid crystal display (LCD) screen, plasma screen, or any other type of screen. The display may be configured to provide a graphical user interface (GUI) rendered through a software application (e.g., via an application programming interface (API) executed on the system). This may include various devices such as touchscreen monitors, joysticks, keyboards and other interactive devices. In some embodiments, a user may be able to provide user input about selecting an algorithm, specifying one or more parameters or image acquisition scheme using a user input device. The user input device can have any type of user interactive component, such as a button, mouse, joystick, trackball, touchpad, pen, image capturing device, motion capture device, microphone, touchscreen, hand-held wrist gimbals, exoskeletal gloves, or other user interaction system such as virtual reality systems, augmented reality systems and the like.

The image generation module 4300 may be implemented as a controller or one or more processors. The image generation module may be implemented in software, hardware or a combination of both. The image generation module may be in communication with the detector module 4200, a user console (e.g., display device providing the UI) or in communication with other external devices. The communication may be wired communication, wireless communication or a combination of both. In some cases, the communication may be wireless communication. For example, the wireless communications may include Wi-Fi, radio communications, Bluetooth, IR communications, or other types of direct communications.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for signal processing, the method comprising:
   (a) obtaining (1) a laser speckle signal from a laser speckle pattern generated using at least one laser light source that is directed towards a tissue region of a subject and (2) a reference signal comprising time series data corresponding to a movement of a biological material of or within the subject's body, wherein the reference signal comprises an externally derived signal associated with one or more signals other than the laser speckle signal;
   (b) comparing one or more pixel values associated with the laser speckle signal against the reference signal by determining a correlation between (i) a first time series associated with the laser speckle signal and (ii) a second time series associated with the reference signal, wherein said comparing is performed in real time and frame-by-frame for each frame captured for a laser speckle image comprising the laser speckle pattern;
   (c) generating one or more output signals in part based on the correlation determined in (b), wherein the one or more output signals are indicative of the movement of the biological material; and
   (d) using the one or more output signals to (i) generate a perfusion flow map for the tissue region of the subject and (ii) eliminate one or more false positives in the perfusion flow map.

2. The method of claim 1, wherein the laser speckle pattern is generated using a plurality of laser light sources configured to generate a plurality of laser beams or pulses having different wavelengths.

3. The method of claim 2, wherein the plurality of laser beams or pulses have a wavelength between about 100 nanometers (nm) and about 1 millimeter (mm).

4. The method of claim 1, wherein the laser speckle signal is obtained or updated over a plurality of frames as the plurality of frames are being received or processed in real time.

5. The method of claim 1, wherein determining the correlation comprises computing at least one of an inner product, a dot product, a cross-correlation, an auto-correlation, a normalized cross-correlation, and a weighted measure integration.

6. The method of claim 1, wherein determining the correlation comprises using one or more signal or time series comparators to determine an amount or a degree of the correlation between the laser speckle signal and the reference signal.

7. The method of claim 1, wherein the comparing of the one or more pixel values associated with the laser speckle signal against the reference signal is performed in a time domain or a frequency domain.

8. The method of claim 1, wherein the comparing of the one or more pixel values associated with the laser speckle signal against the reference signal occurs over at least a portion of a laser speckle image comprising the laser speckle pattern, the portion corresponding to one or more regions of interest in or near the tissue region of the subject.

9. The method of claim 1, wherein the reference signal comprises a pulse signal associated with a pulse of the subject or a movement signal associated with a movement of a tissue of the subject's body.

10. The method of claim 9, wherein the reference signal is obtained or generated using a tool or an instrument.

11. The method of claim 9, further comprising using the reference signal to determine if one or more features of the laser speckle pattern are attributable to a fluid flow or a physical motion.

12. The method of claim 9, wherein the one or more output signals comprise a flow signal or a force signal.

13. The method of claim 1, wherein the one or more false positives correspond to one or more areas in the perfusion flow map that indicate a movement but do not have fluid flowing through the one or more areas.

14. The method of claim 1, further comprising using the one or more output signals to determine an amount of force exerted on a tissue in or near the tissue region of the subject by a tool or an instrument.

15. The method of claim 1, wherein the biological material comprises a fluid or a tissue.

16. The method of claim 1, wherein the externally derived signal is obtained using a pulse monitor or a pulse oximeter.

17. The method of claim 11, wherein the physical motion corresponds to peristalsis, respiration, or camera motion.

18. The method of claim 1, further comprising, subsequent to (c), determining a viability of the tissue region based on the one or more output signals.

19. The method of claim 1, further comprising using at least a subset of the one or more output signals to identify one or more anatomical structures.

20. The method of claim 1, further comprising, subsequent to (d), generating an image overlay comprising the perfusion flow map and one or more images of the tissue region.

* * * * *